(12) United States Patent
Merril et al.

(10) Patent No.: US 7,163,818 B2
(45) Date of Patent: Jan. 16, 2007

(54) BACTERIOPHAGE HAVING MULTIPLE HOST RANGE

(75) Inventors: Carl R. Merril, Rockville, MD (US); Sankar Adhya, Gaithersburg, MD (US); Dean Scholl, Kensington, MD (US)

(73) Assignee: The United States of America as represented by the Department of Health and Human Services, Washington, DC (US)

( * ) Notice: Subject to any disclaimer, the term of this patent is extended or adjusted under 35 U.S.C. 154(b) by 521 days.

(21) Appl. No.: 10/350,256

(22) Filed: Jan. 21, 2003

(65) Prior Publication Data

US 2003/0216338 A1  Nov. 20, 2003

Related U.S. Application Data

(63) Continuation of application No. PCT/US01/23390, filed on Jul. 25, 2001.

(60) Provisional application No. 60/220,987, filed on Jul. 25, 2000.

(51) Int. Cl.
*C12N 7/00* (2006.01)
*C12Q 1/70* (2006.01)
*A61K 39/00* (2006.01)
*A61K 39/12* (2006.01)

(52) U.S. Cl. ............ 435/235.1; 435/5; 435/948; 424/184.1; 424/199.1; 424/204.1

(58) Field of Classification Search ............ 435/235.1, 435/948; 424/184.1, 199.1, 204.1
See application file for complete search history.

(56) References Cited

U.S. PATENT DOCUMENTS

| | | |
|---|---|---|
| 4,405,720 A | 9/1983 | Merril |
| 4,508,820 A | 4/1985 | Merril et al. |
| 4,555,490 A | 11/1985 | Merril |
| 4,703,016 A | 10/1987 | Merril |
| 4,892,814 A | 1/1990 | Harrington et al. |
| 4,940,659 A | 7/1990 | Warrington et al. |
| 5,292,665 A | 3/1994 | Hochstrasser et al. |
| 5,364,793 A | 11/1994 | Cameron, Sr. et al. |
| 5,369,004 A | 11/1994 | Polymeropoulos et al. |
| 5,378,602 A | 1/1995 | Polymeropoulos et al. |
| 5,429,947 A | 7/1995 | Merril et al. |

(Continued)

FOREIGN PATENT DOCUMENTS

WO   WO 96 21007   7/1996

(Continued)

OTHER PUBLICATIONS

Jensen EC, HS Schrader, B Rieland, TL Thompson, KW Lee, KW Nickerson and TA Kokjohn, "Prevalance of Broad-Host-Range Lytic Bacteriophages of *Sphaerotilus natans*, *Escherichia coli*, and *Pseudomonas aeruginosa*" Appl Environ Microbiol. Feb. 1998, p. 575-580.*

(Continued)

*Primary Examiner*—Bruce R. Campbell
*Assistant Examiner*—Stuart W. Snyder
(74) *Attorney, Agent, or Firm*—Knobbe, Martens, Olson & Bear, LLP

(57) ABSTRACT

The present invention discloses compositions and methods for the prophylaxis and treatment of bacterial infections by the use of polyvalent bacteriophage having multiple host range.

3 Claims, 4 Drawing Sheets

U.S. PATENT DOCUMENTS

| | | | |
|---|---|---|---|
| 5,468,610 | A | 11/1995 | Polymeropoulos et al. |
| 5,583,201 | A | 12/1996 | Cameron, Sr. et al. |
| 5,660,812 | A | 8/1997 | Merril et al. |
| 5,688,501 | A | 11/1997 | Merril et al. |
| 5,721,100 | A | 2/1998 | Polymeropoulos et al. |
| 5,766,892 | A | 6/1998 | Merril et al. |
| 5,811,093 | A | 9/1998 | Merril et al. |
| 5,817,797 | A | 10/1998 | Mitchell et al. |
| 5,844,097 | A | 12/1998 | Cameron et al. |
| 5,861,504 | A | 1/1999 | Polymeropoulos et al. |
| 2001/0026795 | A1 | 10/2001 | Merril et al. |
| 2001/0043917 | A1 | 11/2001 | Merril et al. |
| 2001/0043924 | A1 | 11/2001 | Carlton et al. |
| 2002/0150631 | A1 | 10/2002 | Merril et al. |
| 2002/0177614 | A1 | 11/2002 | Merril et al. |
| 2003/0026785 | A1 | 2/2003 | Merril et al. |
| 2004/0132181 | A1 | 7/2004 | Mitchell et al. |
| 2004/0161411 | A1 | 8/2004 | Merril et al. |
| 2004/0161431 | A1 | 8/2004 | Carlton et al. |
| 2005/0063957 | A1 | 3/2005 | Merril et al. |
| 2005/0118567 | A1 | 6/2005 | Merril et al. |

FOREIGN PATENT DOCUMENTS

| | | |
|---|---|---|
| WO | WO 97 29185 | 8/1997 |
| WO | WO 98 05344 | 2/1998 |

OTHER PUBLICATIONS

Altschul, S. F. et al. 1990. Basic local alignment search tool. *J. Mol. Biol.* 215:403-410.

Barrow and Soothill 1997 Bacteriophage therapy and prophylaxis: rediscovery and renewed assessment of potential. *Trends Microbiol.* 5(7):268-271.

Botstein, D. 1980. A theory of modular evolution for bacteriophages. *Ann. N. Y. Acad. Sci.* 354:484-490.

Brown, J. E. et al 1986. Sequences of three promoters for the bacteriophage SP6 RNA polymerase. *Nucleic Acids Res.* 14:3521-3526.

Campbell, A., and D. Botstein. 1983. *Lambda II*, p. 365-380. Cold Spring Harbor Laboratory, Cold Spring Harbor, N.Y.

Cao et al. 2000 Helicobacter pylori-antigen-binding fragments expressed on the filamentous M13 phage prevent bacterial growth. *Biochim Biophys Acta* 1474(1):107-13.

Chandry, P. S. et al. 1997. Analysis of the DNA Sequence, gene expression, origin of replication, and modular structure of the *Lactococcus lactis* lytic bacteriophage sk1. *Mol. Microbiol.* 26:49-64.

Clarke, B. R. et al. 2000. Cloning, expression, and purification of the K5 capsular polysaccharide lyase (KflA) from coliphage K5A: evidence for two distinct K5 lyase enzymes. *J. Bacteriol.* 182:3761-3766.

Crawford, J. T., and E. B. Goldberg. 1980. The function of the tail fibers in triggering baseplate expansion of bacteriophage T4. *J. Mol. Biol.* 139:679-690.

Desiere, F. et al. 1998. Evolution of *Streptococcus thermophilus* bacteriophage genomes by modular exchanges followed by point mutations and small deletions and insertions. *Virology* 241:345-356.

Devereux, J. et al. 1984. A comprehensive set of sequence analysis programs for the VAX. *Nucleic Acids Res.* 12:387-395.

Devine et al. 1989 Occurence of K1, K5 and O antigens in *Escherichia coli* isolates from patients with urinary tract infections or bacteraemia *J. Med. Microbiol.* 30(4):295-299.

Gross, R. J. et al. 1977. Isolation of bacteriophages specific for the K1 polysaccharide antigen of *E. coli*. *J. Clin. Microbiol.* 6:548-550.

Gupta, D. S. et al. 1982. Coliphage K5, specific for *E. coli* exhibiting the capsular K5 antigen. *FEMS Microbiol. Lett.* 14:75-78.

Gupta, D. S. et al. 1983. Enzymatic degradation of the capsular K5-antigen of *E. coli* by coliphage K5. *FEMS Microbiol. Lett.* 16:13-17.

Haggaård-Ljungquist, E. et al. 1992. DNA sequences of the tail fiber genes of bacteriophage P2: evidence for horizontal transfer of the tail fiber genes among unrelated bacteriophages. *J. Bacteriol.* 174:1462-1477.

Hanfling, P. et al. 1996. Analysis of the enzymatic cleavage (beta elimination) of the capsular K5 polysaccharide of *Escherichia coli* by the K5-specific coliphage: a reexamination. *J. Bacteriol.* 178:4747-4750.

Hendrix, R. W. et al. 1999. Evolutionary relationships among diverse bacteriophages and prophages: all the world's a phage. *PNAS USA* 96:2192-2197.

Israel, V. 1978. A model for the adsorption of phage P22 to *Salmonella typhimurium*. *J. Gen. Virol.* 40:669-673.

Jann, K., and B. Jann. 1987. Polysacharide antigens of *E. coli*. *Rev. Infect. Dis.* 9:S517-S526.

Jeng, S. T. et al. 1997. Transcription termination by bacteriophage T3 and SP6 RNA polymerases at Rho-independent terminators. *Can. J. Microbiol.* 43:1147-1156.

Juhala, R. J. et al. 2000. Genomic sequences of bacteriophages HK97 and HK022: pervasive genetic mosaicism in the lambdoid bacteriophages. *J. Mol. Biol.* 299:27-51.

Lederberg J. 1996 Smaller fleas . . . ad infinitum: Therapeutic bacteriophages redux. *PNAS* 93:3167-3168.

Long, G. S. et al. 1995. Complete nucleotide sequence of the gene encoding bacteriophage E endosialidase: implications for K1E endosialidase structure and function. *Biochem. J.* 309:543-550.

Machida, Y. et al. 2000. Structure and function of a novel coliphage-associated sialidase: *FEMS Microbiol. Lett.* 182:333-337.

Merril et al. 1996 Long-circulating bacteriphage as antimicrobial agents. *PNAS* 93:3188-3192.

Monod, C. et al. 1997. The genome of the pseudo T-even bacteriophages, a diverse group that resembles T4. *J. Mol. Biol.* 267:237-249.

Montag, D. et al. 1989. A component of the side tail fiber of *Escherichia coli* bacteriophage can functionally replace the receptor-recognizing part of a long tail fiber protein of unrelated bacteriophage T4. *J. Bacteriol.* 171:4378-4384.

Montag, D. et al. 1990. Receptor recognizing proteins of T-even type bacteriophages. The receptor recognizing area of proteins 37 of phages T4 and Tula and Tulb. *J. Mol. Biol.* 216:327-334.

Neve, H. et al. 1998. Comparison of the lysogeny modules from the temperate *Streptococcus thermophilus* bacteriophages TP-J34 and Sfi21: implications for the modular theory of phage evolution. *Virology* 241:61-72.

Nimmich, W. 1994. Detection of *E. coli* K95 strains by bacteriophages. *J. Clin. Microbiol.* 32:2843-2845.

Nimmich, W. et al. 1991. Two different *E. coli* capsular polysaccharide depolymerases each associated with one of the coliphage ΦK5 and ΦK20. *FEMS Microbiol. Lett.* 82:137-142.

Nimmich, W. et al. 1992. Isolation and characterization of bacteriophages specific for capsular antigens K3, K7, K12, and K13 of *E. coli*. *Int. J. Med. Microbiol. Virol. Parasitol. Infect. Dis.* 276:213-220.

Petter, J. G., and E. R. Vimr. 1993. Complete nucleotide sequence of the bacteriophage K1F tail gene encoding endo-N-acylneuraminidase (endo-N) and comparison to an endo-N homolog in bacteriophage PK1E. *J. Bacteriol.* 175:4354-4363.

Schicklmaier, P., and H. Schmeiger. 1997. Sequence comparison of the genes for immunity, DNA replication, and cell lysis of the P22-related *Salmonella* phages ES18 and L.. *Gene* 195:93-100.

Scholl, D. et al. 2001. Bacteriophage K1-5 Encodes two Different Tail Fiber Proteins Allowing It To Infect and Replicate on both K1 and K5 Strains of *Escherichia coli*. *J. Virol.* 75:2509-2515.

Seckler, R. 1998. Folding and function of repetitive structure in the homotrimeric phage P22 tailspike protein. *J. Struct. Biol.* 122:216-222.

Silver, R. P., and E. R. Vimr. 1990. Polysialic acid capsule of *E. coli* K1, p. 39-60. In *The bacteria*, vol. 11. Molecular basis of bacterial pathogenesis. Academic Press, Inc., New York, N.Y.

Steven, A. C. et al. 1988. Molecular substructure of a viral receptor-recognition protein. *J. Mol. Biol.* 200:351-365.

Szybalski, W., and E. H. Szybalski. 1974. *Viruses, evolution and cancer*, p. 563-582. Academic Press, New York, N.Y.

Tetart, F. et al. 1996. Bacteriophage T4 host range is expanded by duplications of a small domain of the tail fiber adhesion. *J. Mol. Biol.* 258:726-731.

Tetart, F. et al. 1998. Genome plasticity in the distal tail fiber locus of the T-even bacteriophage: recombination between conserved motifs swaps adhesion specificity. *J. Mol. Biol.* 282:543-556.

Tomlinson, S., and P. W. Taylor. 1985. Neuraminidase associated with coliphage E that specifically depolymerizes the *Escherichia coli* K1 capsular polysaccharide. *J. Virol.* 55:374-378.

Yin, J. 1993. Evolution of bacteriophage T7 in a growing plaque. *J. Bacteriol.* 175:1272-1277.

* cited by examiner

US 7,163,818 B2

SEQUENCE LISTING

```
<160> NUMBER OF SEQ ID NOS: 4

<210> SEQ ID NO 1
<211> LENGTH: 5518
<212> TYPE: DNA
<213> ORGANISM: Bacteriophage k1-5

<400> SEQUENCE: 1
ggtaggtctt ggtgtagacc ttggctctgg cacggaatcc tctgtgacag atgtggtctg      60
ccaagtgatc acctgtgaat aagtttctag aagttctggc aggtcttatt ggcctgcttg     120
tctctgctaa gaagaaacaa gaagagaagg aggcacaaag tgaagcgaat catgttagtg     180
acaacccttc tgattggttc gctgaccact tccgggtgtc agcaggcgtt accagagaaa     240
gcaatggtga aacctctgag gccgacgctg acggcagttt acgaggtaga cgataaggtc     300
tgctttagta agcctgacgc tacaaaactt ggtttgtaca ttctctcgct agaacgcgga     360
tacaattaat acatagcttt atgtatcagt gtcttacgat ttactggaca ctatagaaga     420
ggtaagatag cgccgttctt ttgagcggcc tattactagc caatcttcat agggagggtt     480
ggaaagtaat aggagatagc atggctaaat taaccaaacc taatactgaa ggaatcttgc     540 ataaggaca atctttgtat gagtaccttg atgcgagagt tttaacatca aagccgtttg     600
gtgctgcagg tgacgccact actgatgata cggaggttat agctgcttca ttaaactctc     660
agaaagctgt cacagtctca gatggtgtat tctctagctc tggtattaac agtaattact     720
gtaacttaga cggcaggggt agtggcgtgc taagtcaccg ttcaagtaca ggtaactact     780
tagtatttaa caatctacgt gcaggtcgct taagtaatat tacggtagaa agtaataagg     840
cgactgatac aactcaggga cagcaggtat cccttgctgg tggaagtgat gttactgtaa     900
gtgacgttaa cttctcaaac gttaaggta ctggtttcag tttaatcgca taccctaatg      960
atgcgccacc tgatggactt atgattaaag gcattcgagg tagctattcc ggctatgcta    1020
ctaataaggc agccggatgc gtacttgctg attcctcagt taactccctc atagataacg    1080
```

-continued

| | | | | | |
|---|---|---|---|---|---|
| tcattgctaa | gaactaccct | cagttcggag | cagtagagtt | gaaaggtaca | gccagttaca | 1140 |
| acatagtcag | taatgttata | gggacagatt | gccagcatgt | aacttacaac | ggcactgaag | 1200 |
| ggccaatagc | tccttctaat | aaccttatca | aggggggtgat | ggctaataac | cctaagtatg | 1260 |
| cagcggttgt | tgcaggcaaa | ggaagtacga | acttaatctc | agacgtgctc | gtagattact | 1320 |
| caacttctga | tgctaggcag | gctcatggtg | ttacagtaga | gggttctgat | aacgtcataa | 1380 |
| ataatgtgct | tatgtcagga | tgtgatggta | ctaactcttt | aggacaaggg | cagactgcta | 1440 |
| caattgcacg | ctttataggt | acagctaata | caaactatgc | gtctgtattt | cctagctaca | 1500 |
| gtgctacagg | tgttattact | ttcgaatccg | gctctacccg | taacttcgta | gaggtaaagc | 1560 |
| accctggcag | gagaaacgac | cttctcagtt | ctgctagtac | tattgacggt | gcagctacta | 1620 |
| ttgacggcac | tagtaatagt | aacgtagtgc | acgcacctgc | cttagggcag | tacataggta | 1680 |
| gtatgtcagg | taggttcgaa | tggcggatta | agtccatgtc | actcccttca | ggcgttctta | 1740 |
| cttctgctga | taagtacaga | atgcttggag | atggtgctgt | gtcattagct | gtaggtgggg | 1800 |
| gcacttcttc | tcaagttcgc | ctatttactt | ctgatggtac | ttctcggaca | gtgtccctca | 1860 |
| ccaacggtaa | cgtgcgtctt | tctaccagta | gcacaggctt | tttgcagtta | ggtgctgatg | 1920 |
| caatgacccc | agacagtact | ggtacatacg | cattaggttc | cgccagccga | gcatggtctg | 1980 |
| gcggttttac | tcaagcagca | ttcactgtta | cctcagatgc | tcggtgtaaa | acagaacctc | 2040 |
| ttactatctc | agatgcctta | ctggatgctt | ggtctgaagt | tgactttgtg | cagtttcagt | 2100 |
| atttggatcg | tgttgaggag | aagggtgcag | actcagctag | atggcacttc | ggtatcatcg | 2160 |
| ctcagcgagc | taaggaggct | ttcgaacgtc | acggtataga | tgcacatcgc | tatggcttct | 2220 |
| tgtgcttcga | cagttgggat | gatgtatacg | aggaagatgc | caatggctct | cgtaaactga | 2280 |
| ttacaccagc | aggttcccgc | tacggtattc | gttacgagga | agtactgata | ttagaggctg | 2340 |
| cgttgatgcg | gcggactatt | aagcgtatgc | aggaagcact | agcttccctg | cctaagtaag | 2400 |
| caacaggcag | tgcgtaagca | ctgcttttag | cgcaacttttt | cttaaaggtt | atcacggtgg | 2460 |
| tagcctttca | gaaaaggagg | ttacatgatt | caaagactag | gttcttcatt | agttaaattc | 2520 |
| aagagtaaaa | tagcaggtgc | aatctggcgt | aacttggatg | acaagctcac | cgaggttgta | 2580 |
| tcgcttaaag | atttttggagc | caaaggtgat | ggtaagacaa | acgaccaaga | tgcagtaaat | 2640 |
| gcagcgatgg | cttcaggtaa | gagaattgac | ggtgctggtg | ctacttacaa | agtatcatct | 2700 |
| ttacctgata | tggagcgatt | ctataacacc | cgcttcgtat | gggaacgttt | agcaggtcaa | 2760 |
| cctctttact | atgtgagtaa | aggttttatc | aatggtgaac | tatataaaat | cacggataac | 2820 |
| ccttattaca | atgcttggcc | tcaagacaaa | gcgtttgtat | atgagaacgt | gatatatgca | 2880 |
| ccttacatgg | gtagtgaccg | tcatggtgtt | agtcgtctgc | atgtatcatg | ggttaagtct | 2940 |
| ggtgacgatg | gtcaaacatg | gtctactcca | gagtggttaa | ctgatctgca | tccagattac | 3000 |
| cctacagtga | actatcattg | tatgagtatg | ggtgtatgtc | gcaaccgtct | gtttgccatg | 3060 |
| attgaaacac | gtactttagc | caagaacaaa | ctaaccaatt | gtgcattgtg | ggatcgccct | 3120 |
| atgtctcgta | gtctgcatct | tactggtggt | atcactaagg | ctgcaaatca | gcaatatgca | 3180 |
| acaatacatg | taccagatca | cggactattc | gtgggcgatt | ttgttaactt | ctctaattct | 3240 |
| gcggtaacag | gtgtatcagg | tgatatgact | gttgcaacgg | taatagataa | ggacaacttc | 3300 |
| acggttctta | cacctaacca | gcagacttca | gatttgaata | acgctggaaa | gagttggcac | 3360 |
| atgggtactt | ctttccataa | gtctccatgg | cgtaagacag | atcttggtct | aatccctagt | 3420 |
| gtcacagagg | tgcatagctt | tgctactatt | gataacaatg | gctttgttat | gggctatcat | 3480 |

```
caaggtgatg tagctccacg agaagttggt cttttctact tccctgatgc tttcaatagc   3540
ccatctaatt atgttcgtcg tcagatacca tctgagtatg aaccagatgc gtcagagcca   3600
tgcatcaagt actatgacgg tgtattatac cttatcactc gtggcactct tggtgacaga   3660
cttggaagct cttttgcatc gtagtagagat ataggtcaga cttgggagtc actgagattt   3720
ccacataatg ttcatcatac taccctacct tttgctaaag taggagatga ccttattatg   3780
tttggttcag aacgtgcaga aaatgaatgg gaagcaggtg caccagatga tcgttacaag   3840
gcatcttatc ctcgtacctt ctatgcacga ttgaatgtaa acaattggaa tgcagatgat   3900
attgaatggg ttaacatcac agaccaaatc tatcaaggtg acattgtgaa ctctagtgta   3960
ggtgtaggtt cggtagtagt taaagacagc tacatttact atatctttgg tggcgaaaac   4020
catttcaacc caatgactta tggtgacaac aaaggtaaag acccatttaa aggtcatgga   4080
caccctactg atatatactg ctataagatg cagattgcaa atgacaatcg tgtatctcgt   4140
aagtttacat atggtgcaac tccgggtcaa gctatacctz ctttcatggg tactgatgga   4200
atacgaaata tccctgcacc tttgtatttc tcagataaca ttgttacaga ggatactaaa   4260
gttggacact taacacttaa agcaagcaca agttccaata tacgatctga agtgcagatg   4320
gaaggtgaat atggctttat tggcaagtct gttccaaagg acaacccaac tggtcaacgt   4380
ttgattattt gtggtggaga agagacttcg tcctcttcag gtgcacagat aactttgcac   4440
ggctctaatt caagtaaggc taatcgtatc acttataacg gaaatgagca cctattccaa   4500
ggtgcaccaa tcatgcctgc tgtagataac cagtttgctg ctggtggacc tagtaaccga   4560
ttcactacca tctacctagg tagtgaccct gttacaactt cagatgctga ccacaagtac   4620
agtatctcta gtattaatac caaggtgtta aaggcttgga gcagggttgg ttttaaacag   4680
tatggtttga atagtgaagc agagagggac cttgatagca tacacttcgg tgtcttggct   4740
caggatattg tagctgcttt tgaagctgaa gggttggatg ccattaagta tggaattgtg   4800
tccttcgaag aaggtaggta cggtgtgagg tatagtgaag ttctaatact agaggctgct   4860
tatactcgtt atcgtttaga caagttagag gagatgtatg ccactaataa aatcagttaa   4920
gcaagctgct gtactccaga acacagaaga gcttattcaa tcaggacgtg accctaagca   4980
ggcttatgcc attgccaagg atgttcaacg tcgtgccatg aagaaacctt ctgcatcttc   5040
tgcgtaagca ggttaatatc ttagtataaa caagggcaga cttaggtttg tccttagtgt   5100
attccaaagg aggtaaacatg ctgaaagatg gttgggtttc atatgaccct acagaccota   5160
agaattggct acaggttatc gctatagctt gtgcaggtag cctattggct gccctgatgt   5220
attcattatg gatgtacaca aagtaaccaa agtcaaaatt ttgatgtagg cgtgtgtcag   5280
ctctctcgcc ctcgccctcg ccgggttgtc cccatagggt ggcctgaggg aatccgtctt   5340
cgacgggcag ggctgatgta ctccttgtct agtacaaggg aggcggaggg aacgcctagg   5400
gaggcctagg aatggcttag tggtggacaa ggtgattacc ttagtgaagc ctcttagtgc   5460
attcctgagg ccattcaggg cgtttatgag ggattgacag ggtgtgaggg cgtgggct    5518
```

<210> SEQ ID NO 2
<211> LENGTH: 2211
<212> TYPE: DNA
<213> ORGANISM: Salmonella phage Sp6
<220> FEATURE:
<221> NAME/KEY: misc_feature
<222> LOCATION: (1)...(2211)
<223> OTHER INFORMATION: n = A,T,C or G

<400> SEQUENCE: 2

```
aagttttcca attaatacat aaccttatgt atcatacaca tacgatttag gtgacactat      60
agaatagaag tatagtgccg ttcttttgag cggcctatta ctcaccagtc ttcacgggga     120
gggctggata gtaataggag gtttatgtca ttaactaaac cacgttgctt caggaaggca     180
agttatctaa gccagttagg cactttgcag aatctggcta acactggaga tgacgtactt     240
gttatcgatg ttgactacaa gttcaccaat ggagagactg tagacttcaa aggtcgattg     300
gttcgtatag aatgcgaagc tagattcata ggcgatggag ctttaatttt cactaatatc     360
gctagtggtt ctgtagtaga aaagcctttc atggagagca agtccacacc ttgggttatc     420
taccccttgga cagaagatgg caagtggatt acagatgcac aagctgttgc tgctacgctt     480
aaacaatcta agaccgaagg atatcaacct ggagtcaatg attgggtcaa gttcccagga     540
cttgaagcat tgataccgca agaggtgaaa gaccagtatg tagtatcaac actggacatc     600
cgtgattgtg taggtgttga ggttagacgt gctggtgggc ttatggcagc ttacttgttc     660
cgcaactgtc atcattgtaa ggtaattgat tctgacacca tcattggtgg taaagacggc     720
atcataacct ttgaaaactt aggtggtgaa tggggtatcg gcaactatgc cataggtggt     780
cgtgtacatt atggctcatg tagtggtgtg cagtttcttc ggaacaatgg aggtgcatca     840
cataatggtg gagttattgg tgtgacctca tggcgcgcag gtgagtctgg gtttaaaaca     900
tggcaaggtt ctgtaggtgc aggtacatct cgtaactata accttcagtt ccgtgactca     960
gttgcattat ctccagtatg ggacggcttt gacttaggct cagaccctgg aatggcacca    1020
gaagaggata gaccgggaga tttacctgta tctcaatacc ccatgcacca gttacctaat    1080
aaccacatgg ttgataacat acttgttatg aactcattag gtgtaggttt aggtatggac    1140
ggtagaggtg gttatgtgtc gaatgttacc gtgcaggatt gtgcaggcgc aggtatactt    1200
gctcatgcat tcaaccgtac cttctctaac attacggtga ttgactgcaa ctacatgaac    1260
ttcgattcag accagataat catcattggt cactgcatcg tgaatggcat ccgagcagcg    1320
ggtattaagc ctcagccatc caaaggcatg atcatcagtg cacctcactc aaccttgagc    1380
ggtattgtgg gtaatgtgcc gccagaccgt attcttgcag gtaacatcct tgaccctgtg    1440
ttgggtcata caaggattaa tgggtttaat agtgactcgg cggaactgag cttcagaatc    1500
cacaagctta ccaagacctt ggatagtggt gctattcgct ctacgctgaa cggtgggccg    1560
ggtactggtt ctgcatggac tgagatgact gcaatttcag ggtcagctcc aaatgctgtc    1620
tcgttgaaga ttaaccgagg agacttcaag gcaactgaga taccagtagc acctactgtg    1680
cttccagatg aagcggtaag agaccacagc tctatcgcac tttattttga tcaggaagct    1740
cttttgggctt tagttaagaa gccgaacgga agcctcacac gaatgaagct tgcttaatgt    1800
aggcagcgcg ttagcgctgc tttcacgcga acttttctta aaggttatca tagtggtagc    1860
cttttcagaaa aggaggtgac atgatacaaa gattaggttc ttccttagtg aagatgccaa    1920
atggtattac attgacacag tggttgcaac ctgcaaacat catcaaggta gatgatgcac    1980
catacaatgg agaccttatt gctgcatata atgctattcc cgtttataggt aattatgctt    2040
tggttcttac caaccacact tacaatgcag ttggtttgtt tgatgcaggt ccgtaacatg    2100
aagcctaaca tcaccatcat tggtgctggt atgcctcaac ttgcagatga taggtcgtcc    2160
tttgttgaaa gntctggcac tatcattaaa ggcgcaatca agaacttccg c             2211
```

<210> SEQ ID NO 3
<211> LENGTH: 9643

-continued

```
<212> TYPE: DNA
<213> ORGANISM: Bacteriophage K1-5
<220> FEATURE:
<221> NAME/KEY: misc_feature
<222> LOCATION: (1)...(9643)
<223> OTHER INFORMATION: n = A,T,C or G

<400> SEQUENCE: 3
ttcgtcgctg cggtagcctg atgtgtacct taggttattc cttgatggat agcttaggtt      60
agccttagtg gattacctta gttaaagcct tagtgcttca cttagtatca gcttagtagt     120
gtaccttagt aagtcttagt gtcttctctt agtgattgca catgcnagca tgtaagatgc     180
taataggtcg cggtcggcag accgctaaag aaagagaatg gtaataagat gcagtaggag     240
gaacaccaga agcctagcca acctaagcta tcctagctct atatctattg cttttcctta     300
gtctaacacg ttagacaacc tatcttattc ttagtgatgg taacttagtg ttgacaagat     360
aatcttagtg taatactatg catcacgtag gcggtgctga ggcacctagt agccagctag     420
taaggcatac gaagagacta gcgcttacat tgctctttaa caatttgctt agtgtaacct     480
atgtatgccg tggttaacta cttattgaat gaggtattaa ctatgacatt aaataaccgt     540
gaactgtccg ttctcttcac tctgttgtgc tacatgattc gtaacaacga attacttaca     600
gatgatgagt tagccttgta tcaccgcttt cttaacgaag gttggaccga tacagttaat     660
caataccgta acatgataga tgagttgagg gagggtaaat aatgtatcaa catgaggtat     720
tctttgaatc agctagcgaa gctattcgct tccgtgatga tatgatgcaa gctggtgtag     780
gcgttgatgt gtatcactat ttgatagatt acgacactga atatcaccga gttaccttag     840
tatctgagta tgacaaccaa gtcattactg agtatctagg cagtgaagat tacgattacg     900
atgaagtaat cacgacaaat ctctaaatta actgttgaca gccacggcat acaaggttac     960
attaagcatc aagacggcga cgtctttaaa catcccgctc tttaacaata cggtttgtgt    1020
cttgataggc taactaacta actaaggtaa ttatcatgaa agggttaatt tgtgtagaac    1080
gtatggtcaa tggtaaactt gaaatattac cactggaaaa ccaatctagc ttcaaagagt    1140
ggtatggctg tttctcactg atttaaggta aaggctggca ctagtcagcc tatcaaggcg    1200
caaaccaagc tctttaacaa tttggatggt agcttcttag tctggatagg ttaaacctag    1260
gagattctct tgagtctcct ataatgtaac ctaactaact aaatgaggat taaatcatgg    1320
aacgcaatgc taacgcttac tacaaccttc tggctgcaac tgttgaagca ttcaacgagc    1380
gtattcagtt tgatgagatt cgcgaaggtg atgattactc tgatgcacta catgaggttg    1440
tagacagcaa tgttccagtt tattacagcg aaatctttac agtgatggct gctgatggta    1500
ttgatgttga ttttgaggat gctggtttga ttcctgacac gaaggatgta accaagattc    1560
tacaagctcg catctatgaa gctctttata atgatgtacc aaatgacagc gatgtagttt    1620
ggtgtgaagg cgaagaagag gaagaataag gatggaaaag caatataact ttatcttttc    1680
agacggtgta accctgaagt gttccctacg attcgcacaa attcgtgagg aagtactagg    1740
cactacatac aaactatttta gctgacacta taagagaagg cttaacaagg cgttactaag    1800
gtagcgcctg attaaacttt cacttactag gagttgagat tatgaaaacc ttgattggat    1860
gcttcttgtt ggcttctctt gctctggcat ttaccgctaa agctggttat gacgcttata    1920
aagtagaaca agcccagcaa gactgggcca aaaaaaagtt caacttgtgc agcaagagca    1980
acacctacga gtactgcaac aaaacactaa gacacttatg gaaagagtaa ctagcctata    2040
gcccacctga gtgggctatg tgatatttac ttaacactat ataaggtgat tactatgact    2100
```

```
actgaaaaca ccctcgtgtc tgtccgtgaa gctgcaaccg ctgaaatcaa gcaacattta    2160
gacaatatcg gcacttctta catcaaagta ggggcttgtc tgaatgagtt acgcggagac    2220
tttgaaggtc aaaagagtt tttagcctat gttgaagcag agtttgccat taagaaggca    2280
caatgttaca agctgatgag tgtagcccgt gtctttgaag gcgatgatcg ctttaaaggc    2340
gtggcgatgc gtgtaatgct ggcgcttgtt cctttcgctg atgaaaatat aatcatggag    2400
aaggccgcag aactcgccgc aaatggcaag ctggacacta atgccgtaaa cgccctgatt    2460
gaacctaaga aagagtcaaa ggccgaaacg gtacaatcta aggctgagac agtaaaaccg    2520
caggagaacg cgactgagtc cgcagaatca catgaaatgc aagcgccgca ggtagtgcca    2580
cccgcgagcg agcaggagtc cgacgaatca gcaccttggg aagaggaaag caaaccggaa    2640
gcgccaaagg cagctccgat ggataacacg gctaatactg agaatgccgc tattgctggt    2700
ctgctggcac aaattaaagc actgactgag caattacagg cagccaatga ccgcatcgcc    2760
tccttaagta gcgcacgcga aagcaagaag gcatccgcac ctatgctgcc gcagttcaaa    2820
tcttcctgct tctacgctcg cttaggcttg agcgcggagg aggcaacgaa gaaaacagca    2880
gttaacaagg cacgccgcga actggttaag ctgggatacg tgaaggcca tgaggcatgg    2940 cccttaatct ctgaggcagt agaagagttg actaagtaac cttatcggtg gcatcttctt    3000
aggtgtcacc tattaaggtt tctttcacta ggagtaaaca agatgcaagg cctacacgct    3060
attcaacttc aacttgaaga agaaatgttt aacggcggta tccgtcgctt tgaagcggac    3120
caacaacgcc agattgcatc cggtaatgaa tcagacacgg catggaatcg ccgcttattg    3180
tccgagttaa tcgcgccaat ggctgaaggt attcaggcat acaaggaaga gtatgaaggt    3240
aaaagaggcc gtgcaccgcg tgcattagct ttcattaact gcgtagaaaa cgaagtggca    3300
gcatatatca cgatgaaaat cgttatggat atgctgaaca cggatgtaac cttgcaggct    3360
atagccatga atgtagctga ccgcattgag gaccaagtac gttttagcaa gctggaaggt    3420
cacgccgcca aatactttga aaaagttaag aagtcactta aggcaagtaa gactaaatca    3480
tatcgccatg cgcacaacgt agcggtagtg gctgagaagt cagtagctga ccgtgacgct    3540
gatttctccc gctgggaggc atggcctaaa gacaccttgc tgcaaattgg gatgaccttg    3600
cttgaaatct tagagaatag cgtattcttc aacgggcaac ctgtcttcct ccgcaccttg    3660
cgcactaatg gcggcaaaca tggtgtttac tacctacaga ctagtgaaca cgtaggtgag    3720
tggataactg cattcaaaga gcacgtagcg caactgagtc ctgcctatgc tccttgcgtc    3780
atccctccgc gtccgtgggt atcaccttt aacggcggtt tccacactga gaaagtagca    3840
agcccgtatt cgtctggtaa aaggaaaccg cgaacacgtc cgcaagctga ccaaaaagca    3900
aatgccagag gtttacaagg ctgttaacgc gttgcaggcg actaaatggc aggttaacaa    3960
ggaagtttta caggttgtgg aagacgtcat ccgtctagac ctaggttatg gtgtaccttc    4020
cttaaaccca ctcattgacc gcgagaacaa gccagctaat ccagtgccgc tagaatttca    4080
gcacctacgg ggccgtgaac tgaaagaaat gcttacgccg gaacaatggc aagcctttat    4140
caactggaaa ggtgaatgta ctaagctgta caccgctgaa actaagcgcg gaagcaaatc    4200
ggcggcaacc gttcgcatgg ttggtcaggc ccgtaaatat agccagttcg acgcaatcta    4260
cttcgtgtat gcactggaca gccgcagccg cgtctacgcg caatctagca cactctcacc    4320
gcaatcaaat gacttgggca aggccttgct ccgtttttacc gaagggcagc gtcttgatag    4380
cgctgaggcg cttaagtggt ttttggtgaa cggggctaat aactgggtt gggataagaa    4440 aactttgac gtgcgcaccg ctacgtgctg gatagtgaat ttcaagacat gtgccgcgac    4500
```

-continued

```
attgcagcgg atccgctgac cttcactcaa tgggtaaatg ccgactcccc ttacggcttc    4560
cttgcatggt gctttgaata tgcgcgttat ctggatgcac tggatgaagg cacgcaagac    4620
caattcatga cgcacctccc agtccatcaa gatggtagtt gttctggtat ccagcactac    4680
agtgctatgc tacgcgatgc agtaggtgcg aaagcagtaa accttaagcc ctctgactct    4740
cctcaagata tttatggtgc cgttgcgcag gtagtaattc agaagaatta tgcatacatg    4800
aatgcagagg atgcggaaac cttcacttct ggcagcgtga ctttaacagg tgcggagctg    4860
cgtagtatgg ctagtgcgtg ggatatgata ggaatcactc gcggcctgac caaaaagccc    4920
gtaatgacac taccttatgg cagcacacgt ctaacctgcc gtgagtcagt gattgattat    4980
atcgttgatt tagaagaaaa agaggcccaa cgggctattg cggaagggcg taccgccaat    5040
cctgtacacc cttttgataa tgaccgtaaa gacagcctga cacctagcgc agcttataac    5100
tatatgacag ctttaatctg gccttctatt tcggaagtgg ttaaagcccc tatagtggca    5160
atgaaaatga ttcgtcagct tgcccgtttc gcagctaaaa ggaatgaagg cttagagtat    5220
accctgccta ctggcttcat cttgcaacaa aagattatgg ctactgatat gctccgcgta    5280
tctacttgct tgatgggaga atcaagatg agtctacaga ttgaaacaga cgtagtggat    5340
gaaacggcaa tgatgggcgc tgctgctcct aactttgtgc atggtcatga tgccagccac    5400
cttatcttaa cagtctgcga ccttgttgat aaagggatta catctatcgc agttattcat    5460
gactcttttg gcactcatgc aggccgtaca gccgaccttc gtgatagctt aagggcagaa    5520
atggtgaaga tgtatcaagg ccgtaatgca ctgcaaagcc tgctagatga gcacgaagaa    5580
cgctggttag ttgataccgg aatacaagta ccagagcaag gggagtttga ccttaacgaa    5640
atcttagttt cagactattg cttcgcataa tattaatagg ccattccttc gggagtggcc    5700 tttctttttac ctactacctg taacatttca ttaacataaa agtgtctcac atgtgagact    5760
tatttaccgg acactatagg atagccgtcg gagacgggaa agaaagggaa gataaaggat    5820
ataaaggaag taataggtat taaaggttat ataggttatc taggaatacc tattaccttc    5880
ttccttcctc ttattaccac tcagaggaag ggcagaccta ggttgtctca catgtgagac    5940
ttcgtattta ccggacagta tagataagat taactcactt tggagattta accatgcgca    6000
actttgagaa gatggcccgt aaagctaacc gttttgacat ggaagagggg cagaagaaag    6060
gcaagaagct gaataagcct gtccgtgacc gtgcatctaa acgcgctgcg tgggagttct    6120
aagttatggc tattattcag aatgtaccgt gtcctgcctg tcaaaagaat ggacatgata    6180
ttactggcaa ccatctcatg atatttgatg atggtgccgg ctactgtaat cgtggacact    6240
ttcatgataa tggtagacct tactatcaca agccggaagg tggcatcgag ataaccgagt    6300
tatctattac tggcaatatc aaatatacac cttctcaatt caaagaaatg gagaaggaag    6360
ggaagataag cgaccctaaa ttacgtgcca tcgcacttgg tggtatgcgt atgaaagacc    6420
gttgggaggt catgaatgaa caagaagggg cagagcaaga agcagagtgg aaacttgatg    6480
ttgaatggtt cctcacgctt aagcgtaaga accttgtttc caggcacatt cgcggcgaca    6540
tttgcgcatt gtatgatgta cgtgttgggc acgatgaaga gggtagagtc tcacggcatt    6600
actatccgcg cttcgaaaaa ggtgagctag taggcgctaa gtgtcgcaca ttacctaaag    6660
attttaagtt tggtcatttg gtaaactct ttggtatgca agatctttt ggtatgaata    6720 ctttgtctca cgtgttagac aagggaagac gaaaggattg cttgctcatt gtcggcggcg    6780
aactggatgc actagcagcg cagcagatgc tccttgattc tgccaagggt actaagtggg    6840
```

-continued

```
aaggccagcc ataccatgta tggtctgtca acaaaggcga gtcttgcctt gaagagatag      6900
tgcagaaccg tgagcatatc gcccaattca agaagattat atgggttttt gatggagatg      6960
aggtagggca gaagcagaat cagcaagcgg ctcgcctgtt tcctggtaaa tcctatatcc      7020
ttgaataccc ctctggttgc aaagatgcta acaaggcatt gatggctggc aaggctaaag      7080
aatttgtaga tgcatggttt aatgccaagt catctgatga agtctttggt agccagatta      7140
aatctatcgc atctcaaagg gataagctca aggctgcacg tccagagcaa ggactgtcat      7200
ggccttggcc taagctgaac aaggtaacgc taggtattcg taagaaccag cttatcattg      7260
taggtgcagg tctggtgta ggtaagactg agttccttcg tgaagtagtt aagcacctca      7320
ttgaagaaca cggtgaatct gtaggcatca tttctacaga agacccgatg gtcaaggtgt      7380
cccgtgcttt tatcggcaag tggattgata agcgtattga gttacctcca accaacgacc      7440
cgaaagaaga cggataccgt gaggtgttcg actataccga ggaagaagct aacgccgcca      7500
ttgattatgt agctgataca ggtaagctgt ttgtagctga cctagagggt gactattcga      7560
tggaaaaggt agagcaaact tgcctagagt ttgaggctat gggtatttct aatatcatca      7620
ttgataactt aacggggatt aaattagatg agcgtgcttt tggtgggaag gttggtgcac      7680
ttgatgaatg cgtcaagcgg attggtacta tcaaagaccg acaccggtt actatattcc       7740 ttgtatcaca ccttacacgt cctccggcaa accgtaccca acgaagaa ggtggcgaag         7800 ttatcctttc tgacttccga ggctcaggcg ctatcggatt ctgggcatct tacgccttgg      7860
ggattgagcg taatacaaga gctgaaacgc ttgacgaaag gactaccacg tacatctcat      7920
gtgtcaaaga ccgcgaccaa ggtatctaca ctggaaccaa ggtcatgctt aagggtgaca      7980
ttcaaaccgg acgtttaatg gaaccacaag cccgtactaa gtcatttgat acaggtgaag      8040
caaggcaaca agaagtacca gatttaccgg atactataga agagactacc ttcgatgaag      8100
aaagtgagtt ctgattagtg tatttatcag gcttgtctca catgtgagac aggctcttat      8160
taagtacatt aaataactgg agattgatta tgtataactt agtgttgaat gtaggtgact      8220
ttgtacgcaa catcaagaaa gattcaagtc gctatctttg ccgtggtgtt gtaacctttg      8280
taggtgagaa cctgtattat gtagaatatc gcagtggtgt taagcaatat taccacaaga      8340
agacagcaca taaatatctt gaaaagattg tagagataaa caatcaatgt aagtgcatac      8400
atgatgaggt ttgcgataaa tgtgctcgcc agatgcttaa gaatttccta gctcctcttt      8460
attatggtgc tggtcctcaa acactagcag agtgcatggc agaaaagaaa accacactca      8520
agaaagagcg tcgcaatgta atcactggta agactcaaag tgagatgatt aagcaatgtg      8580
gcactgcatt aggtgttaca cagtttaata ctcgtgcatt gggtaaatcc acaggacaag      8640
ctatggtaaa gattggagaa gccatgatgc atccaaatgt acctgtgcga atcatggatg      8700
ttgaccatgc aatcacagaa caaggtacgc aacgacgtgt aattaataag cattttgccg      8760
acactataga aggcattatt cgtaagcaag ggttgaaagg tcttcacatc ttaaatggtg      8820
aagaattact gtacctacct atcgttactg aagaaacata cgtgaatatc taaggagtta      8880
atcatgacta aggtattaat ttatatgcgt ggacctcata aatgctatgc agttgtagca      8940
ccaaatggtg ttaagcctta tcgtacttca aaaagattgg cattaatagg tgctagtagt      9000
agtgcaagtt tccaaatgga acttttggt cattggactg aaaggcaatt ccgtgaggat       9060
tttaaagtca ttgcagctt catggtgaaa tatgcagaat aaacatagtc ttagaatgtt       9120
cgatggtcat gaaaacctgc aagccaagat tactaaccaa gccttcctgt tcgcacagtt      9180
aactatggct gaggctaaga agaatagtct cactcgtgaa caggttatca aggaggccac      9240
```

-continued

```
ttgggaacca caccaaggta aatatatggg ccacaaatta actgtaacac gcagtcgata      9300
agtcaagggt tgtccaacgt gttggacagc ctttcatcat attgattggg aggtattaaa      9360
tgactaagtt tactatgcaa gacctcatta aattacgtga tgaaatagaa tcaccggaag      9420
ttaatacaga gtttcactac attgatccac gagataaacg agagattcct gattatcaga      9480
ttgagacgga gttaatgtat gaagattatt gattggaaga aggaagcaga aggccgtatc      9540
ctagngatgg atgcggaggc taaaggcctg ctgggtgcta tccgctacgg tcatcgtgaa      9600
gatgtacaca ttatttgctg catggacttg ctcaccactg agg                       9643

<210> SEQ ID NO 4
<211> LENGTH: 14226
<212> TYPE: DNA
<213> ORGANISM: Bacteriophage K1-5
<220> FEATURE:
<221> NAME/KEY: misc_feature
<222> LOCATION: (1)...(14226)
<223> OTHER INFORMATION: n = A,T,C or G

<400> SEQUENCE: 4
gcacaagagc ctatgccagn ttaaccaact gccaaagata ttggtaaatt tggactagct        60
aacttcctca tgtcttctgc ttttngcttc tggtgagaat ctgccttcta acttcgagat       120
taactatcga ggtaatatgc aacaattcta tgacaagcta gctatggatg agaataaaga       180
taaagttggc tttaataagg caactggaac ctttactcca tataaagacg ctcacggtga       240
gtctatcggt tacggtcatt tcttaacgga agaagagaag cgaaacgggt atattaagat       300
tggcgatgaa ctagttccct atcgagggtc tatgtctcag cttacagaga gcaaggctcg       360
cgctcttatg gagcaagatg ctaagaagca tgtgcctcct actcgtgact ggaagattcc       420
gtttgaccag atgcaccctg cacagcaacg tggcttgatg gatttaagct acaatttagg       480
taaaggtgga atccagaact caccgcgtgc tcttgctgca ttcaaagctg gtaagcttac       540
ggagggcttt atcgaaatgc tgggcactgc atcaagtgaa ggtaagcgta ttcctggcct       600
actgaagcga cgcgctgagg catacaatat ggcatctgct ggtggtgtgc ctaagattac       660
cgaagtggag actcgtgaag atggctccat gtgggttagg tttggtggac ctatgccagc       720
aggttctgtc tcggcatgga ctcataaacg tattggcgcg gatggttggt atcaggttta       780
tgaggctgca cctaccaagt tagctaaaga ttctaaggta ggtaaagtta agttgtagta       840
cctaactcaa ggcttgtctc acatgtgaga caggtcttta tgataggcac tatggaggaa       900
ttatggaaca agacattaag actaattggg ctggatatgt ccagtctact cctgagccgt       960
tttctattga ggcggctccg gtatcggctc ctacgatacg ccagcgtaat gagttacaag      1020
agcaagttct tgaagctaaa gctgacgctg atatcttagg tgctgtaggt gctgccttcc      1080
agaatgagtg gttggcattc ggaggcaagc ggtggtatga ccgtgccact gctgatttca      1140
cacctcaacc agactttgag atacaacctg agcaacgtga agcactacgt ttcaaatatg      1200
gtacggatat gatgcagaca atcactgagg gtgttcgttc tgaggatgaa ttgaacttcc      1260
gtattcagaa tgcggatgaa gaccttgagc gcaataagcg cattgctcag gctggctggg      1320
ttggctctgt ggcgacgatt ggcgctgctg tgcttgaccc tgtgggatgg ttgcctctca      1380
ttccaaccgg tggtgccgct aaagttggac tcgtaggccg tgctgtgcgt ggcgctatcg      1440
ccgctggcgt gagtaatgcc gctattgaat ccgtattggt ccaaggtgac atgactcgtg      1500
atttagatga cattatggta gcactgggtt ccggtatggc tatgggtggc gttattggcg      1560
```

-continued

```
ctgtagcgcg tggtagggcc actaagctca gtgagcaagg tgatgacagg gctgctagca    1620
ttgtgcgcag tgcagacgca ggggaccgct atgttcgtgc tgttgccgat gacagtatcg    1680
gtgcgatgcg tgttaagggc gcagaggttc tcactgaggg tgtattcgat atctccagta    1740
agagtgaaga cctactgaaa accttgcaac gagaaggtaa tgcgattgat atgacacctc    1800
gccgttgggc tggaactatg tctgccctcg gtactgtcgt gcactcatct aaagatgcaa    1860
gtatccgagg ccttggtgct cgtctgtttg aatccccaca aggtctaggt atgcagaagg    1920
catctgctag tcttatgcag aatactaact taaatcgcct gaaatctgct gatatgaacc    1980
gcttcaatga tgggtttgat tgtggctta agagaataa tatcaatcca gtagcagggc    2040
ataccaactc tcattatgta cagcaataca atgaaaaggt gtgggaggca gtgcgtattg    2100
gcatggatga gtctacacct aaatctatcc gcatggctgc tgagggacaa caggctatgt    2160
acagagaggc gctggcttta cgtcaacgtt ctggtgaagc gggatttgaa aaggtaaaag    2220
ccgacaacaa atatatgcct gatatctttg atagtatgaa agccagacgt caattcgata    2280
tgcacgataa agaagacatc atcgaacttt tctctcgtgc ctaccagaat ggcgctcgta    2340
agattccaaa ggaagcagca gatgagattg cacgagcaca ggtaaatcgc gttgctgatg    2400
ctaccttaac tggaaagctt agttttgaaa aggcaatgtc aggtcagact aaggcagagt    2460
atgaagctat catgcgtaag gcaggcttca gtgatgaaga aattgaaaag atgatagaag    2520
ctctggataa caaagaaacc agagataaca tctctaaccg agctaaaatg agtttaggat    2580
tagatgttac tcaagaatac aatggcattc gtatgcgtga cttcatgaat accaacgtgg    2640
aagagctaac agataactat atgaaggaag cagcaggtgg cgctgcattg gctcgccaag    2700
gcttctctac ctatcaggct gcacttaatg caattgacct tgtagagcga atgcacgaa    2760 acgcggctaa ggatagcaag gctagtttgg cattagatga agagattcgt cagatgcgag    2820
aaggtcttcg cctgattatg ggcaagtcga ttgatgcaga cccacaggct atatctacta    2880
agatgatgcg tcgtggtcgt gatatcacag gtgtgcttcg cttaggtcaa atgggcttcg    2940
cacagctagg tgaacttgcc aactttatgg gtgaatttgg tattgctgca actactatgg    3000
ctttaggtaa gcaattccgc ttcacctcta aggcgttgcg taatggcgat ggcttcttcc    3060
gagataagaa cttagctgag gttgagagaa tggtggggta cattggtgag gataactggc    3120
taacaactaa gggtgcacgt cctgatgaat ttggtgatgt aaccacagta agagggatga    3180
tggctcactt tgaccaatcc atgaactcaa tacgtcgtgc tcaaaccaac ctatcactct    3240
tccgcatggc acaggttct ctggagcgaa tgactaatag gcaaatagct ttgtctttca    3300
ttgaccacct tgaaggcaag aagattattc ctcagaagaa actggaggaa cttggtctta    3360
ctcaggagtt catgactaac ctacagaagc actatgatgc taactctaaa ggttctggct    3420
tgcttggctt tgatacaatg ccttatgcca tgggtgaaac tttagctaat gctattcgtc    3480
gtaagtcagg tctaatcatc caacgtaact tcattggtga tgaaggtatc tggatgaaca    3540
aagcactagg taagacattt gcacagctta agtcattctc tcttgtatct ggtgagaagc    3600
aatttggtcg agggattcgc cacgataaaa ttggtcttgc taagaagaca gcttacgggt    3660
ttgctttggg ttcaatagtg tatgcggcaa agcctatgt gaactctatt gggcgagaag    3720
accaagatga atatttggaa gagaagttat cgcctaaagg gttggccttt ggtgcaatgg    3780
gtatgatgag tacaactgct gtatttagtc taggtggaga tttcttaggt ggcctaggtg    3840
ttctaccttc cgaactcatt caatcacgct atgaagcagg tttccaaagt aagggtctga    3900
ttgaccaaat acctctggtt ggcgttggtg cagatgcagt aaatctggct aactcaatca    3960
```

-continued

| | | | | | |
|---|---|---|---|---|---|
| agaagtatgc | agaaggtgac | acagaaggtg | tagatatcgc | taagcgagca | ctccgtcttg | 4020 |
| tgccacttac | caatataata | ggtgtccaaa | acgcattgcg | ttatggctta | gatgaactgg | 4080 |
| aggattgatg | agttatactt | tcacagaaca | tacagccaat | ggtacgcaag | tcacctatcc | 4140 |
| ttttagcttt | gctggtaggg | ataaaggtta | tcttcgtgcc | tcagatgtga | tagtggagtc | 4200 |
| tcttcaaggt | aacacttgga | ttgaagttac | atctggctgg | caactaactg | gcacgcacca | 4260 |
| gattactttt | gatgtagcac | cagttgcagg | tttgaagttc | cgtattcgaa | gggaagtaca | 4320 |
| aaaagaatat | ccatacgctg | agtttgaccg | tggtgttacc | ttggatatga | agtctttaaa | 4380 |
| tggttctttc | attcatatac | tggagattac | acaggagtta | cttgacgggt | tttatccaga | 4440 |
| aggatacttc | attaaacaga | atgtaagctg | gggcggcaat | aagattactg | atttggctga | 4500 |
| tggcacaaat | ccgggagatg | cagtaaataa | agggcagctt | gatgccatcg | acaagaagca | 4560 |
| tacagattgg | aacgccaaac | aggacattga | gattgctggc | cttaaggctg | gtatgacttc | 4620 |
| tggtattgcg | cacagaactg | ttccttggta | cacgatagcc | caaggtggtg | agatttccgt | 4680 |
| aaaaccacct | tatgaatttc | aagatgcact | agttttcctt | aatggggtat | tgcagcacca | 4740 |
| aattgtaggc | gcatactcta | taagcaacaa | cactatcact | ttcgcagagc | cgcttgtggc | 4800 |
| tggtacagag | gtgtatgtgc | tgattggtag | tcgtgtggct | acatctgaac | ctaatattca | 4860 |
| gttggagttg | aactttgact | tagtagaagg | ccaacaagta | gtacagattg | gctctgcatt | 4920 |
| taagtacatt | gaggtctacc | ttgatggatt | attacaacct | aaacttgctt | atcaggtaga | 4980 |
| cggtgacatt | gttactttct | cagaaagagt | accagaatgc | cggatgactg | ctaagattat | 5040 |
| cacagcataa | ggaggtggga | tgattaactc | cgaactggta | gatagtggtg | tgaagcttgc | 5100 |
| gccacctgca | ctcatatcag | gtgggtactt | cctcggtatc | agttgggata | attgggtgtt | 5160 |
| aatagcaaca | ttcatttata | ccgtgttgca | aattggggac | tggttttata | ataagttcaa | 5220 |
| gatttggagg | gagaagcgtg | agcgtacaca | ataaacatgc | agctacagag | gacgaggttg | 5280 |
| gcattctgca | tggtgctatt | accaaaatct | tcaataagaa | agcacaggca | atactggaca | 5340 |
| ctatagaaga | agaccctgat | gcagcattac | atttagtgtc | tggtaaggat | attggtgcga | 5400 |
| tgtgtaagtg | ggttcttgat | aacggcatta | ccgccacacc | tgctgcacag | caggaagagt | 5460 |
| ccaagttatc | taagcgcctc | aaggctatcc | gagaggcatc | cagtggtaag | ataattcaat | 5520 |
| tcactaagga | ggattgatgg | ctaaggcaag | agaatcacaa | gcggaggctc | ttgccagatg | 5580 |
| ggagatgcta | caggagttac | agcagacctt | tccttacacc | gcggaaggtt | tgcttctctt | 5640 |
| tgcagataca | gttattcata | acttaattgc | aggcaaccct | catctgattc | gtatgcaggc | 5700 |
| ggatatcttg | aagttcctat | tttacggaca | caagtaccgc | ctcatcgaag | cgcctcgtgg | 5760 |
| tatcgctaag | acaacactat | cagcaatcta | tacggtattc | cgtattattc | atgaaccgca | 5820 |
| taagcgtatc | atggttgtgt | cccaaaacgc | caagcgagca | gaggaaatcg | caggttgggt | 5880 |
| agttaaaatc | ttccgtggct | tagactttct | tgagtttatg | ctgccggata | tctacgctgg | 5940 |
| ggaccgtgca | tccgttaagg | cgtttgagat | tcattacacc | ctacgtggta | gtgataagtc | 6000 |
| tccttctgta | tcctgttact | caatcgaagc | aggtatgcag | ggtgctcgtg | ctgatattat | 6060 |
| tctagcggat | gacgtagagt | cgatgcagaa | tgctcgtacg | gcagcgggcc | gtgccttgct | 6120 |
| tgaggagctg | actaaggagt | ttgaatctat | caaccagttt | ggggatatca | tttaccttgg | 6180 |
| tacacctcag | aacgtaaaact | ctatctacaa | caacctacct | gctcgtggtt | actctgttcg | 6240 |
| tatctggact | gcgcgttacc | cttcagtaga | gcaagagcaa | tgttatggcg | acttccttgc | 6300 |

-continued

```
acctatgatt gttcaagata tgaaggacaa cccagcactt cgctcagggt acgggttgga    6360
tggtaatagt ggtgcacctt gtgccoctga aatgtatgat gatgaagtcc tgattgagaa    6420
ggaaatctct cagggtgctg ctaagttcca gcttcagttc atgcttaaca ctcgcatgat    6480
ggatgctgac agatacccat tacgcctgaa caatctaatc ttcacctcgt ttggtacaga    6540
ggaagtccct gtgatgccta cgtggagtaa tgattccata acatcattg gtgatgcacc     6600 taagtatggt aacaagccta cggatttcat gtacagacct gtagctcgcc catatgaatg    6660
gggtgctgtc tcccgcaaga ttatgtatat tgaccctgcg ggtggtggta agaacggaga    6720
tgagacgggt gtagccatcg tattcctgca cggcacattg atttatgtgt atcagtgctt    6780
tggtgtacct ggcggatacc gagagtcgtc cctgaatcgc attgtgcagg ccgcaaagca    6840
ggcgggtgtt aaagaggtat tcattgagaa gaactttggt catggcgcgt ttgaggcggt    6900
aattaagccg tactttgaac gagagtggcc tgtaactctg aagaggatt acgccaccgg     6960 acagaaagag ttgcgtatca ttgagacgct ggagccgctc atggcagccc ataggcttat    7020
cttcaatgca gagatggtga agtcagactt tgagtcggta cagcactatc cgcttgaact    7080
acgcatgtcc tacagtcttt tcaatcaaat gtcgaacata acgattgaga gaacagcct     7140 ccggcacgat gaccgcctag acgccctgta tggcgctata cggcaattaa cttctcagat    7200
agactatgac gaggttacac ggattaatcg cctcagagcg caggagatgc gcgattacat    7260
ccatgctatg aacacacctc atctacgcag ggcaatgcta tatggagatt acggtactga    7320
gcgaagagtg accaacactt ccgtagcgat gcagcagcga gtttacgggc agaactaccg    7380
aaataaatcg gcaagcagaa atacactttc tgcaaggatt tcaaggactt attaattact    7440
ggacactata gaaggaaggc ccagataata agagaaaata ataggtaata tatatagg     7500 ttaacctagg ttatataggt atgccttagt atgggtgtac tcctgtacac cctattcctt    7560
actaccttac tatatttaca aataggaga gagacaatgg ctaatgatta tagtagtcaa      7620
ccattaacag gtaagtctaa gagaaagcag gtacaacctg taagtgaaga actaatgctt    7680
ccggtgctca aaaagagga agttagtaag aaaagcaatg ttattaatga tgccaccaaa     7740
tcaggtaaac agaaagggc catggtgtgc cttgaagtga aggtggtgt attgaagatt       7800 gctatcgcgg ttgatggcaa agaagattca gagtggaagt tagtaacagt ggaaccaact    7860
gttaacccag tttaagataa ggaggaagat tacatggcta aatatggtac tacaggttct    7920
gttactggtc aggcttttcg agtaaaagca gtacaaacta ttgcaacggc aatcccgatg    7980
cctgttgtta agaagaaga ccttaagagt aaagaccacc ctatcaacat caaacattta     8040
tcaggtaaac agaaaggtgc aatggttgct cttgagaaag gtgacacaac cttacatatt    8100 gctgttcac gtggtagtga acccacagac ccttgggatg taactggtat ggaaaaggac     8160
gctgttactc cagcaggggt ataataatgc ttaataaata cttcaagcgt aaagagtttg    8220
cttgccgttg tgggtgcggt acatccactg ttgatgctga attactacag gtagtcacag    8280
atgtgcgtga gcactttggt tctcctgtag ttatcacttc gggtcatcgc tgtgctaagc    8340
acaatgccaa tgtaggtggc gctaagaact ccatgcatct tactggtaag gctgctgaca    8400
ttaaagtgtc tggcatatta ccttctgaag tgcataagta tcttactagc aaataccaag    8460
gcaagtatgg tataggtaag tataactcct tcactcacat cgatgtacgg gatggttgtg    8520
cgcgatggta agatgtgttg aatggtgtga gcgtatggtt gcccaagctg ccgaggatgg    8580
caactatgat gactggaaga actactctga cttgttagct caatgaaaag ggagatgcaa    8640
tgaaaaagct gtttaagtct aagaaggttg taggtgcact ggttgcactt gttattgctc    8700
```

```
ttgtttctgt aggtcttggt gtagaccttg gctctggcac ggaatcctct gtgacagatg   8760
tggtctgcca agtgatcacc tgtgaataag tttctagaag ttctggcagg tcttattggc   8820
ctgcttgtct ctgctaagaa gaaacaagaa gagaaggagg cacaaagtga agcgaatcat   8880
gttagtgaca acccttctga ttggttcgct gaccacttcc gggtgtcagc aggcgttacc   8940
agagaaagca atggtgaaac ctctgaggcc gacgctgacg gcagtttacg aggtagacga   9000
taaggtctgc tttagtaagc ctgacgctac aaaacttggt ttgtacattc tctcgctaga   9060
acgcggatac aattaataca tagctttatg tatcagtgtc ttacgattta ctggacacta   9120
tagaagaggt aagatagcgc cgttcttttg agcggcctat tactagccaa tcttcatagg   9180
gagggttgga aagtaatagg agatagcatg gctaaattaa ccaaacctaa tactgaagga   9240
atcttgcata aaggacaatc tttgtatgag taccttgatg cgagagtttt aacatcaaag   9300
ccgtttggtg ctgcaggtga cgccactact gatgatacgg aggttatagc tgcttcatta   9360
aactctcaga aagctgtcac agtctcagat ggtgtattct ctagctctgg tattaacagt   9420
aattactgta acttagacgg caggggtagt ggcgtgctaa gtcaccgttc aagtacaggt   9480
aactacttag tatttaacaa tctacgtgca ggtcgcttaa gtaatattac ggtagaaagt   9540
aataaggcga ctgatacaac tcagggacag caggtatccc ttgctggtgg aagtgatgtt   9600
actgtaagtg acgttaactt ctcaaacgtt aaaggtactg gtttcagttt aatcgcatac   9660
cctaatgatg cgccacctga tggacttatg attaaaggca ttcgaggtag ctattccggc   9720
tatgctacta ataaggcagc cggatgcgta cttgctgatt cctcagttaa ctccctcata   9780
gataacgtca ttgctaagaa ctaccctcag ttcggagcag tagagttgaa aggtacagcc   9840
agttacaaca tagtcagtaa tgttataggg acagattgcc agcatgtaac ttacaacggc   9900
actgaagggc caatagctcc ttctaataac cttatcaagg gggtgatggc taataaccct   9960
aagtatgcag cggttgttgc aggcaaagga agtacgaact aatctcaga cgtgctcgta  10020
gattactcaa cttctgatgc taggcaggct catggtgtta cagtagaggg ttctgataac  10080
gtcataaata atgtgcttat gtcaggatgt gatggtacta actctttagg acaagggcag  10140
actgctacaa ttgcacgctt tataggtaca gctaataaca actatgcgtc tgtatttcct  10200
agctacagtg ctacaggtgt tattactttc gaatccggct ctacccgtaa cttcgtagag  10260
gtaaagcacc ctggcaggag aaacgacctt tcagttctg ctagtactat tgacggtgca  10320
gctactattg acggcactag taatagtaac gtagtgcacg cacctgcctt agggcagtac  10380
ataggtagta tgtcaggtag gttcgaatgg cggattaagt ccatgtcact cccttcaggc  10440
gttcttactt ctgctgataa gtacagaatg cttggagatg gtgctgtgtc attagctgta  10500
ggtgggggca cttcttctca agttcgccta tttacttctg atggtacttc tcggacagtg  10560
tccctcacca acggtaacgt gcgtcttttct accagtagca caggcttttt gcagttaggt  10620
gctgatgcaa tgacccccaga cagtactggt acatacgcat taggttccgc cagccgagca  10680
tggtctggcg gttttactca agcagcattc actgttacct cagatgctcg gtgtaaaaca  10740
gaacctctta ctatctcaga tgccttactg gatgcttggt ctgaagttga ctttgtgcag  10800
tttcagtatt tggatcgtgt tgaggagaag ggtgcagact cagctagatg gcacttcggt  10860
atcatcgctc agcgagctaa ggaggctttc gaacgtcacg gtatagatgc acatcgctat  10920
ggcttcttgt gcttcgacag ttgggatgat gtatacgagg aagatgccaa tggctctcgt  10980
aaaactgatta caccagcagg ttcccgctac ggtattcgtt acgaggaagt actgatatta  11040
```

```
gaggctgcgt tgatgcggcg gactattaag cgtatgcagg aagcactagc ttccctgcct    11100
aagtaagcaa caggcagtgc gtaagcactg cttttagcgc aacttttctt aaaggttatc    11160
acggtggtag cctttcagaa aaggaggtta catgattcaa agactaggtt cttcattagt    11220
taaattcaag agtaaaatag caggtgcaat ctggcgtaac ttggatgaca agctcaccga    11280
ggttgtatcg cttaaagatt ttggagccaa aggtgatggt aagacaaacg accaagatgc    11340
agtaaatgca gcgatggctt caggtaagag aattgacggt gctggtgcta cttacaaagt    11400
atcatcttta cctgatatgg agcgattcta taacacccgc ttcgtatggg aacgtttagc    11460
aggtcaacct ctttactatg tgagtaaagg ttttatcaat ggtgaactat ataaaatcac    11520
ggataaccct tattacaatg cttggcctca agacaaagcg tttgtatatg agaacgtgat    11580
atatgcacct tacatgggta gtgaccgtca tggtgttagt cgtctgcatg tatcatgggt    11640
taagtctggt gacgatggtc aaacatggtc tactccagag tggttaactg atctgcatcc    11700
agattaccct acagtgaact atcattgtat gagtatgggt gtatgtcgca accgtctgtt    11760
tgccatgatt gaaacacgta ctttagccaa gaacaaacta accaattgtg cattgtggga    11820
tcgccctatg tctcgtagtc tgcatcttac tggtggtatc actaaggctg caaatcagca    11880
atatgcaaca atacatgtac cagatcacgg actattcgtg ggcgattttg ttaacttctc    11940
taattctgcg gtaacaggtg tatcaggtga tatgactgtt gcaacggtaa tagataagga    12000
caacttcacg gttcttacac ctaaccagca gacttcagat ttgaataacg ctggaaagag    12060
ttggcacatg ggtacttctt tccataagtc tccatggcgt aagacagatc ttggtctaat    12120
ccctagtgtc acagaggtgc atagctttgc tactattgat aacaatggct tgttatggg    12180 ctatcatcaa ggtgatgtag ctccacgaga agttggtctt ttctacttcc ctgatgcttt    12240
caatagccca tctaattatg ttcgtcgtca gataccatct gagtatgaac cagatgcgtc    12300
agagccatgc atcaagtact atgacggtgt attataccct atcactcgtg gcactcttgg    12360
tgacagactt ggaagctctt tgcatcgtag tagagatata ggtcagactt gggagtcact    12420
gagatttcca cataatgttc atcatactac cctacctttt gctaaagtag agatgacct    12480 tattatgttt ggttcagaac gtgcagaaaa tgaatgggaa gcaggtgcac cagatgatcg    12540
ttacaaggca tcttatcctc gtaccttcta tgcacgattg aatgtaaaca attggaatgc    12600
agatgatatt gaatgggtta acatcacaga ccaaatctat caaggtgaca ttgtgaactc    12660
tagtgtaggt gtaggttcgg tagtagttaa agacagctac atttactata tctttggtgg    12720
cgaaaaccat ttcaacccaa tgacttatgg tgacaacaaa ggtaaagacc catttaaagg    12780
tcatggacac cctactgata tatactgcta taagatgcag attgcaaatg acaatcgtgt    12840
atctcgtaag tttacatatg gtgcaactcc gggtcaagct atacctactt tcatgggtac    12900
tgatggaata cgaaatatcc ctgcaccttt gtatttctca gataacattg ttacagagga    12960
tactaaagtt ggacacttaa cacttaaagc aagcacaagt tccaatatac gatctgaagt    13020
gcagatggaa ggtgaatatg gctttattgg caagtctgtt ccaaaggaca acccaactgg    13080
tcaacgtttg attatttgtg gtggagaaga gacttcgtcc tcttcaggtg cacagataac    13140
tttgcacggc tctaattcaa gtaaggctaa tcgtatcact tataacggaa atgagcacct    13200
attccaaggt gcaccaatca tgcctgctgt agataaccag tttgctgctg gtggacctag    13260
taaccgattc actaccatct acctaggtag tgaccctgtt acaacttcag atgctgacca    13320
caagtacagt atctctagta ttaataccaa ggtgttaaag gcttggagca gggttggttt    13380
taaacagtat ggtttgaata gtgaagcaga gagggacctt gatagcatac acttcggtgt    13440
```

```
cttggctcag gatattgtag ctgcttttga agctgaaggg ttggatgcca ttaagtatgg    13500
aattgtgtcc ttcgaagaag gtaggtacgg tgtgaggtat agtgaagttc taatactaga    13560
ggctgcttat actcgttatc gtttagacaa gttagaggag atgtatgcca ctaataaaat    13620
cagttaagca agctgctgta ctccagaaca cagaagagct tattcaatca ggacgtgacc    13680
ctaagcaggc ttatgccatt gccaaggatg ttcaacgtcg tgccatgaag aaaccttctg    13740
catcttctgc gtaagcaggt taatatctta gtataaacaa gggcagactt aggtttgtcc    13800
ttagtgtatt ccaaaggagg taacatgctg aaagatggtt gggtttcata tgaccctaca    13860
gaccctaaga attggctaca ggttatcgct atagcttgtg caggtagcct attggctgcc    13920
ctgatgtatt cattatggat gtacacaaag taaccaaagt caaaattttg atgtaggcgt    13980
gtgtcagctc tctcgccctc gccctcgccg ggttgtcccc atagggtggc ctgagggaat    14040
ccgtcttcga cgggcagggc tgatgtactc cttgtctagt acaagggagg cggagggaac    14100
gcctagggag gcctaggaat ggcttagtgg tggacaaggt gattacctta gtgaagcctc    14160
ttagtgcatt cctgaggcca ttcagggcgt ttatgaggga ttgacagggt gtgagggcgt    14220
gggcta                                                                14226
```

BACTERIOPHAGE HAVING MULTIPLE HOST RANGE

CROSS-REFERENCE TO RELATED APPLICATIONS

This application is a continuation of international application number PCT/US01/23390, and claims the benefit of priority of international application number PCT/US01/23390, having international filing date of Jul. 25, 2001, designating the United States of America and published in English, which claims the benefit of priority of U.S. provisional patent application No. 60/220,987, filed Jul. 25, 2000, both of which are hereby expressly incorporated by reference in their entireties.

FIELD OF THE INVENTION

The present invention discloses compositions and methods for the prophylaxis and treatment of bacterial infections by the use of polyvalent bacteriophage having multiple host range.

BACKGROUND OF THE INVENTION

*Escherichia coli* capsular polysaccharides (K antigens) have often been associated with increased virulence (17). The K1 antigen in particular increases the invasiveness of *E. coli*, and these strains are often involved in cases of meningitis and septicemia (32). These polysaccharide coats also act as recognition sites for bacteriophages, which often carry tail spikes that contain polysaccharide depolymerization activities. Several K1 specific phages have been described (10), one of which, ΦK1E, was found to possess N-acetylneuraminidase (endosialidase) as a part of the tail fiber protein (37). This enzyme catalyzes the cleavage of α-2,8-linked poly-N-acetylneuraminic acid carbohydrate polymer of the K1 capsule. It has been suggested that the tail fiber protein is involved in both adsorption to the cell surface and penetration into the cell by enzymatically degrading the polysaccharide capsule. The ΦK1E endosialidase gene has been cloned and sequenced (20). A similar gene has been cloned and sequenced from ΦK1F (29).

ΦK5 is a related bacteriophage specific for *E. coli* strains that display the K5 antigen, a polymer consisting of a repeating structure of 4-linked a-N-acetylglucosamine and β-glucuronic acid (N-acetyl heparosin). In this case, ΦK5 encodes a tail associated K5 specific lyase protein that is also responsible for attachment to the cell surface and degradation of the K5 polysaccharide capsule (12,14). Phage have also been found that are specific for other *E. coli* polysaccharide antigens including K3, K7, K12, K13, and K20 (26,27); all probably possess specific polysaccharide depolymerization activities as part of the phage particle.

Both ΦK5 and ΦK1E have a *Salmonella* phage SP6-like promoter upstream of their tail proteins as well as a region of sequence similarity, which is just downstream of the lyase gene of ΦK5 and just upstream of the endosialidase gene of ΦK1E (6). The sequences upstream of the tail gene promoters in ΦK1E, and ΦK5 are highly similar as well. ΦK5, ΦK1E and SP6 share a common morphology and life cycle, suggesting that they may be closely related.

Antibiotics superseded the potential use of bacteriophage in the treatment of infections. The extensive use of antibiotics has led to antibiotic-resistant bacterial pathogens. Thus, investigators have reassessed bacteriophage therapy and prophylaxis. However, one major obstacle that is frequently raised to the use of bacteriophage is that of their excessively narrow host range. There is a need for bacteriophage having multiple host-range for use in therapy and prophylaxis.

SUMMARY OF THE INVENTION

A virulent double stranded DNA bacteriophage, ΦK1-5 has been isolated and was found to be capable of infecting *E. coli* strains that possess either the K1 or the K5 polysaccharide capsule. Electron micrographs show that the virion consists of a small icosohedral head with short tail spikes, similar to members of the *Podoviridae* family. DNA sequence analysis of the region encoding the tail fiber protein showed two open reading frames encoding previously characterized hydrolytic phage tail fiber proteins. The first is the K5 lyase protein gene of ΦK5, which allows this phage to specifically infect K5 *E. coli* strains. A second open reading frame encodes a protein almost identical in amino acid sequence to the N-acetylneuraminidase (endosialidase) protein of ΦK1E, which allows this phage to specifically infect K1 strains of *E. coli*. We provide experimental evidence that mature phage particles contain both tail fiber proteins, and mutational analysis indicates that each protein can be independently inactivated. A comparison of the tail gene regions of ΦK5, ΦK1E, and ΦK1–5 shows that the genes are arranged in a modular or cassette configuration. The demonstration that a phage can contain multiple tail proteins that expand its host range is useful in generating phage with broad-spectrum antibacterial properties for therapy and prophylaxis of bacterial infections.

BRIEF DESCRIPTION OF THE SEQUENCES

Figure 1:
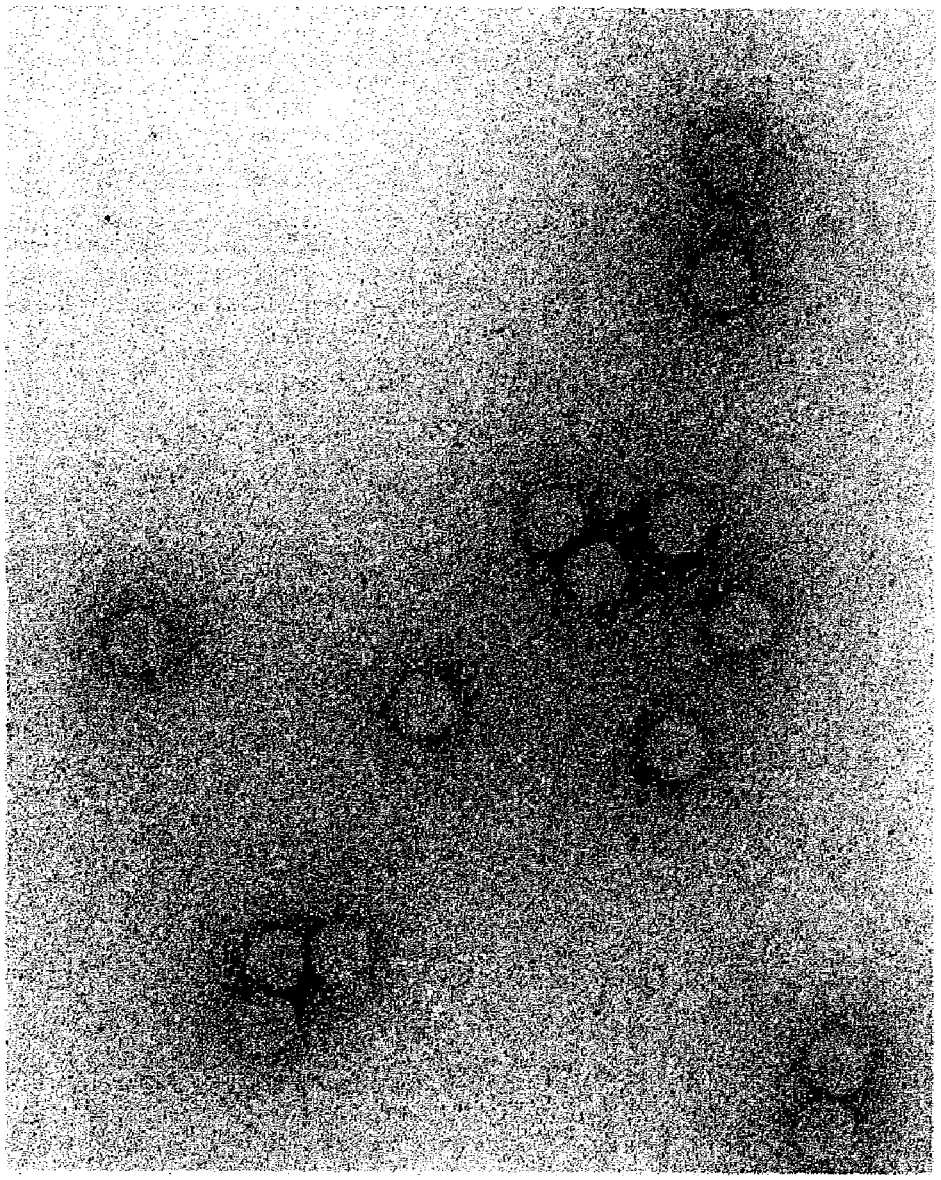
FIG. 1. Electron micrograph of ΦK1–5 negatively stained with phosphotungstic acid at a magnification of X115,500. Morphologically this phage and can be classified in the *Podoviridae* family which includes T7 and SP6.

SEQ ID NO:1 is the DNA sequence of the tail gene region of ΦK1–5.

SEQ ID NO:2 is the DNA sequence of ΦSP6 tail gene.
SEQ ID NO:3 is the DNA sense sequence of ΦK1–5.
SEQ ID NO:4 is the DNA antisense sequence of ΦK1–5.

BRIEF DESCRIPTION OF THE BIOLOGICAL DEPOSITS

Φ1–5 was deposited as ATCC Accession No. PTA-3495 on Jul. 2, 2001 with the American Type Culture Collection (ATCC), 10801 University Blvd., Manassas, Va. 20110–2209, USA. This deposit was made under the provisions of the Budapest Treaty on the International Recognition of the Deposit of Microorganisms for the Purposes of Patent Procedure and the Regulations thereunder (Budapest Treaty). This assures maintenance of a viable culture of the deposit for 30 years from date of deposit. The deposit will be made available by ATCC under the terms of the Budapest Treaty, and subject to an agreement between Applicant and ATCC which assures permanent and unrestricted availability of the progeny of the culture of the deposit to the public upon issuance of the pertinent U.S. patent or upon laying open to the public of any U.S. or foreign patent application, whichever comes first, and assures availability of the progeny to one determined by the U.S. Commissioner of Patents and Trademarks to be entitled thereto according to 35 USC § 122 and the Commissioner's rules pursuant thereto (including 37 CFR § 1.14). Availability of the deposited strain is not to be construed as a license to practice the invention in contravention of the rights granted under the authority of any government in accordance with its patent laws.

DETAILED DESCRIPTION OF THE PREFERRED EMBODIMENT

We have discovered that it is possible to express more than one host specific tail protein in a single bacterial viral strain and that expression of these tail proteins permits the virus to infect multiple specific hosts. This discovery facilitates the genetic engineering of phage with expanded host ranges. For example, there are phage that can infect *E. coli* strains that contain the K1 polysaccharide in their outer capsule. Such *E. coli* bacterial strains are often involved in meningitis and septicemia, as K1 polysaccharide increases the invasiveness of the bacteria (32). A phage (ΦK1E) possesses a tail protein with endosialdase activity that can infect strains of *E. coli* containing the K1 polysaccharide. This endosialdase allows the phage ΦK1E to specifically attach and degrade the K1 polysaccharide (37). Similarly, phage ΦK5 can infect K5 strains of *E. coli*. The K5 strains of *E. coli* are commonly a cause of urinary tract infections (11). The phage ΦK5 contains a tail protein that has lyase activity that allows this phage to attack the bacterial K5 capsule (12, 14). We have demonstrated that it is possible for a phage to have both tail proteins, the K1 endosialdase as well as the K5 lyase. Such a phage, which we have designated phage ΦK1–5, has an expanded host range as it can infect both *E. coli* K1 and *E. coli* K5. We have demonstrated that this expanded host range capability is due to the capacity of this ΦK1–5 phage to display both tail proteins, a K1 endosialidase as well as a K5 lyase. We have demonstrated through sequence analysis of ΦK1–5 phage tail protein genes that they are arranged in a modular or cassette structure, indicating that the host range of phages can be broadened for other K antigens, and even other bacteria species by recombinational techniques. The demonstration that a phage can contain multiple tail proteins that expand its host range is envisioned as being useful in generating phage with broad-spectrum antibacterial properties for the therapy and prophylaxis of infectious diseases. Recently there has been a renewed interest in the use of phages to treat and prevent bacterial infections (for a review see Barrow and Soothill, 1997, *Trends Microbiol.* 5(7), 268–271). ΦK1–5 is highly lytic, non-lysogenic, very stable, and kills bacteria rapidly, all features that make it a good candidate for phage therapy. The phage ΦK1–5 has an additional advantage because it recognizes and attaches to the same structure(s) that confer virulence to the bacteria. In addition, bacteria that become resistant to phage usually have lost the polysaccharide capsule and are no longer virulent. Given these findings, ΦK1–5 is envisioned as being used as a general platform phage for therapeutic and prophylatic applications in which host specificity will be altered by engineering the tail protein genes. The capacity to engineer the expression of tail proteins is also envisioned as providing for phage that can transfer genes to organisms that are not normally infected by phage. Such a goal is to be achieved by expressing a mammalian viral protein on the tail of the phage to enable such a phage to transfer its genetic material into a mammalian cell. Phage with this capability will be of use in gene therapy applications.

Referring to FIG. 1, ΦK1–5 is an isolated bacteriophage consisting of an icosohedral head with a small tuft of short tail fibers that is able to infect and replicate on either K1 or K5 strains of *E. coli*. It appears that its ability to replicate on these strains is due to the fact that it encodes two different hydrolytic tail fiber proteins. One is an endosialidase protein, almost identical to a similar protein from ΦK1E, that allows it to attach to and degrade the K1 polysaccharide capsule. The other is almost identical to a lyase protein that has been shown to allow ΦK5 to attach to and degrade the K5 polysaccharide capsule. This is the first example of a phage that has a dual host specificity based on having two different tail proteins.

Figure 2:
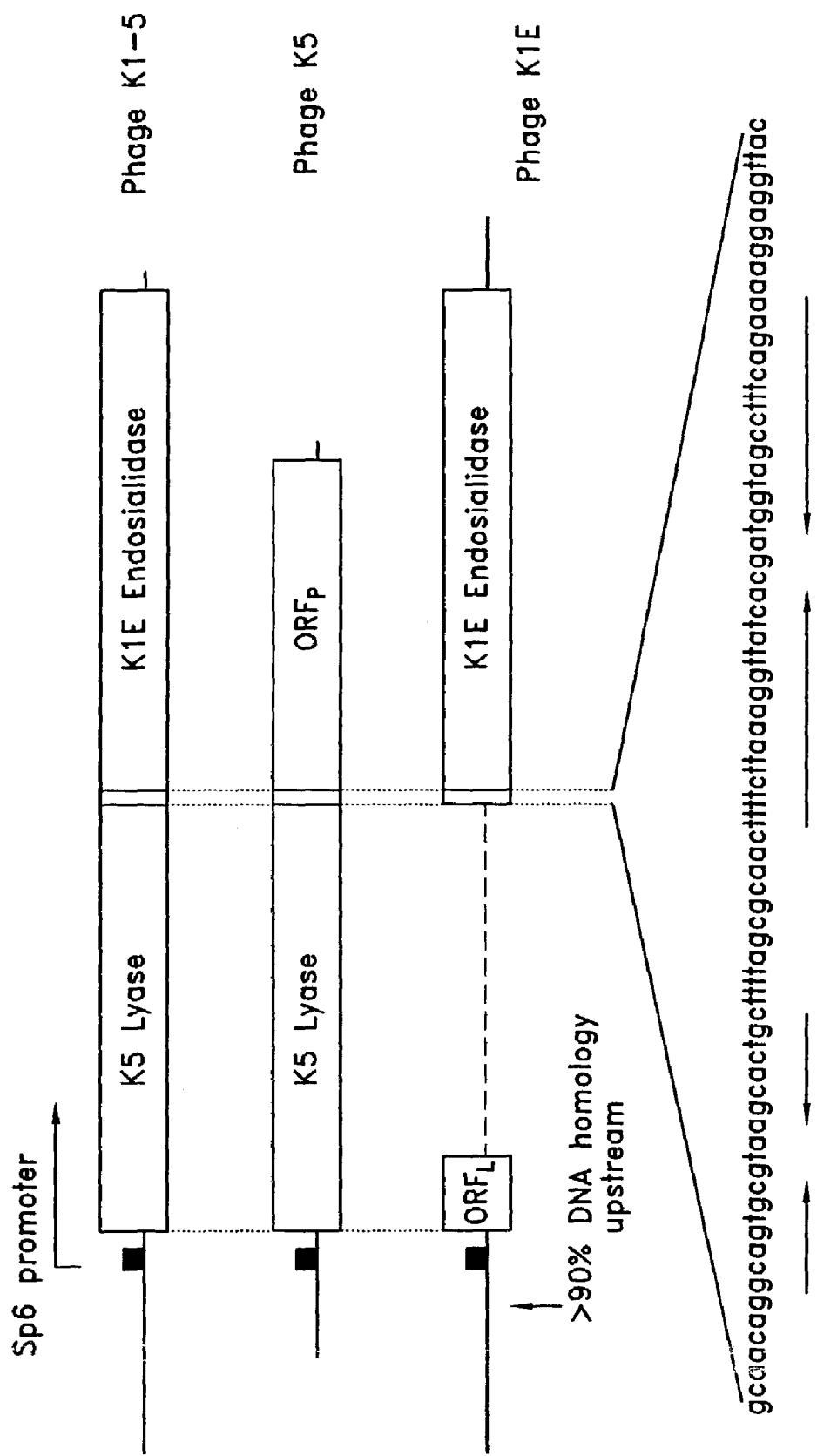
FIG. 2. Comparison of the coding regions of the tail proteins of ΦK1–5, ΦK5, and ΦK1E. All three phages share sequence similarity in the upstream region (which contains an SP6 promoter) as well as an 85-base intergenic region. Just downstream of the promoter, ΦK1–5 and ΦK5 encode a lyase protein and ΦK1E encodes $ORF_L$. Immediately following the termination codons of the lyases or $ORF_L$ is the intergenic region that contains a potential hairpin structure, the first of which could be a Rho-independent transcription terminator. Immediately following this, ΦK1–5 and ΦK1E encode an endosialidase where ΦK5 encodes $ORF_P$. None of the three phages have any coding regions downstream, and the DNA molecule ends in all three cases. No sequence similarity exists in this terminal region.

Referring to FIG. 2, all three of these phages share sequence similarity upstream of the region encoding the tail proteins and all have an ΦSP6-like promoter that probably drives transcription of the tail gene(s). In ΦK1–5 and ΦK5, the first gene downstream of this promoter is the K5 lyase protein. ΦK1E does not encode this protein and instead has a 111 amino acid ORF (ORF$_L$) of unknown function. Immediately downstream of the K5 lyase proteins of ΦK1–5 and ΦK5, and downstream of ORF$_L$ in ΦK1E is an 85 base region of similarity between all three phages. This region contains two strong symmetrical elements that may be involved in transcription termination. Further downstream, phages ΦK1–5 and ΦK1E encode the endosialidase gene. ΦK5 does not encode this gene but instead encodes the 523 amino acid ORF$_P$.

ΦK1–5 is a bacteriophage that we isolated from sewage using a K5 strain of *E. coli* as a host. By analyzing the host range of ΦK1–5, we found that it can replicate on either K1 or K5 strains. DNA sequence analysis of the tail fiber genes revealed that it encodes both a K5 lyase protein similar to that of ΦK5 and an endosialidase protein similar to that of ΦK1E. The arrangement of these genes indicates that phage host range can be broadened or changed by the acquisition of new tail genes by recombination in nature or by technology in the laboratory.

ΦK5 also is able to replicate on K95 strains of *E. coli* (28). Since ORF$_P$ is in a position analogous to that of the endosialidase of ΦK1–5, it is also envisioned as a tail protein responsible for growth on K95 strains. Another K antigen specific phage, ΦK20, is also able to lyse two different types of *E. coli* hosts, those that possess the K5 antigen and those that possess the K20 polysaccharide (26). We envision ΦK20 as carrying a K5 lyase protein similar to the ΦK5/ΦK1–5 protein along with a K20 specific hydrolytic tail protein. Phages have also been isolated that are specific to the capsular antigens K3, K7, K12, and K13 of *E. coli*. Presumably these phages have corresponding K specific hydrolytic tail proteins. We envision other phages having multiple specificities with other combinations of K antigens.

Figure 3A:
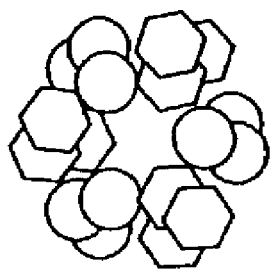
FIG. 3. Two possible models for the arrangement of the tail proteins on the phage capsid. (a) There are three copies of each tail forming a hexamer. (b) There are six copies of each tail. One is attached to the head and is part of the "core" of the tail. The other is then attached to the first tail protein, in effect making a longer tail fiber with two different enzymatic activities.
Figure 3B:
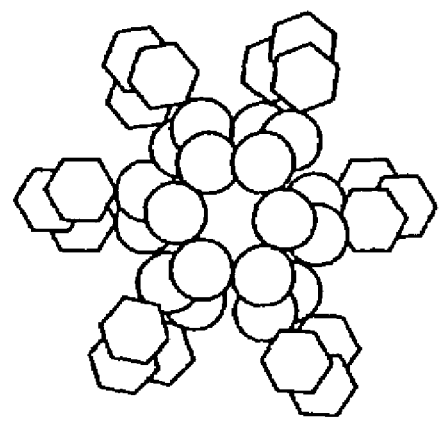

The host range of a bacteriophage is expanded beyond *E. coli* by expressing the genes encoding multiple different host tail proteins, a constraint being an understanding of the mechanism by which the tail protein is attached to the capsid structure of a phage. The N-terminus of the T7 tail protein is thought to be involved in attachment (29). Neither the endosialidase nor the K5 lyase has this region, or any other region similar to any other tail protein (or with each other). Morphologically, ΦK1E, ΦK5 and ΦK1–5, are similar to *Salmonella* phage P22. The tail protein of P22 has been extensively studied and is also a hydrolytic protein involved in degradation of the Salmonella typhimurium O antigen. This protein is a homotrimer with six copies per phage (30). The gp17 tail-fiber of T7 is also a trimer with 6 copies of the trimer per phage particle (33). The endosialidase of ΦK1E is also a trimer (20), but it has yet to be shown that there are 6 copies of the trimer per phage particle. Bacteriophage 63D is another newly characterized sialidase containing phage in which it has been shown by electron microscopy that the sialidase is present with 6 copies per particle (21). This phage is quite different morphologically from ΦK1E, ΦK5, and ΦK1–5 and has a long tail similar to that of bacteriophage lambda, with the sialidase located at the end of the tail. Six copies of a trimeric tail protein appear to be a general structural motif. Assuming that the endosialidase and K5 lyase are also arranged in six copies per virion, it is interesting to speculate how the two tail proteins are arranged on the head structure of ΦK1E. They may be arranged in an alternating fashion where there are three copies of each (FIG. 3*a*). In the case of P22, there is evidence that only three copies of the tail are needed for infection (16) suggesting that this model is theoretically possible. The fact that there are no common sequence similarities between the two tail proteins argues against this model, since one might predict a common motif within the tail proteins that is required to attach to similar regions of the head structure. An alternative model is that there may be 6 copies of each tail protein, one attached to the other (FIG. 3*b*). Since the N-terminus of the T7 tail protein is thought to be involved in attachment of the tail protein to the head structure, this region of the protein and similar regions of other tail proteins (or alternative regions of tail proteins that mediate attachment of one to the other) are envisioned as serving the attachment function, so an understanding of the mechanism no longer acts as a constraint.

Figure 4:
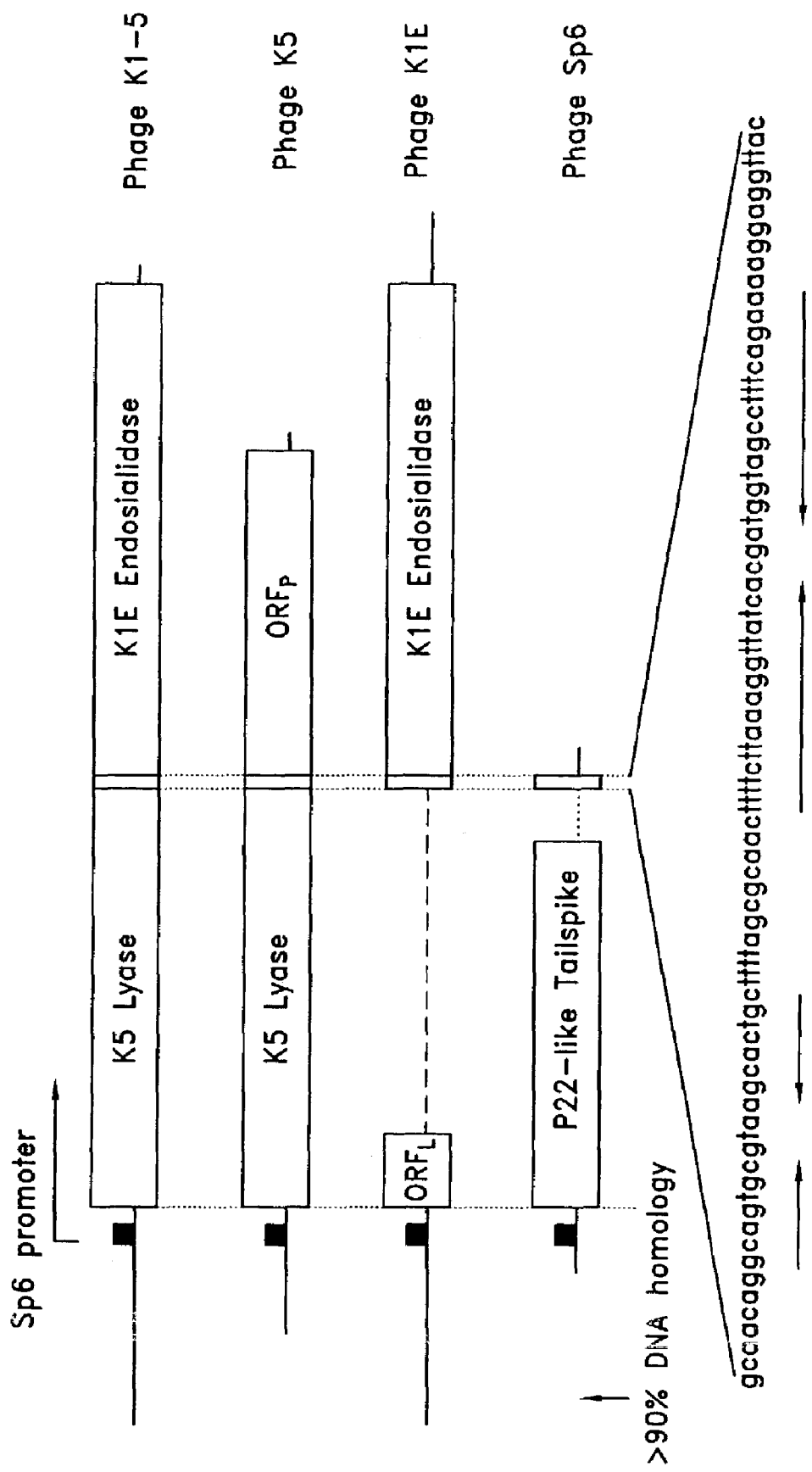
FIG. 4. Comparison of the coding regions of the tail proteins of ΦK1–5, ΦK5, ΦK1E, and SP6.

Our findings indicate that phages ΦK5, ΦK1E, and ΦK1–5 all share a region of sequence similarity upstream of the tail proteins. This region contains a Salmonella phage SP6 promoter. The DNA sequence surrounding the promoter described in Nam et al., Gene 1986, 46:57 matched the analogous sequence in ΦK1–5. Based on this information, we designed a primer from this region to sequence downstream of the analogous region in phage ΦSP6. DNA sequencing identified an open reading frame that has a high degree of amino acid similarity to phage P22 tail protein. ΦP22 is a well characterized *Salmonella* phage that has a similar morphology to ΦSP6, but has a very different life cycle. (ΦP22 is lysogenic like *E. coli* phage lambda, and ΦSP6 is lytic like T7 or the three K antigen phages). The P22 tail protein also has a polysaccharide degradation activity. Immediately downstream of the SP6 tail gene lies the 85 base pair intergenic region common to ΦK5, ΦK1E and ΦK1–5, and shortly after that the DNA molecule ends. FIG. 4 compares the regions encoding the tail proteins in all four phage. The SP6 tail protein is in the analogous position as the lyase protein of ΦK1–5 and ΦK5 and $ORF_L$ of ΦK1E. ΦSP6 shares the cassette structure of the three K phages, indicating that all four are closely related and differ mainly in the tail proteins. We envision replacing the lyase protein of ΦK1–5 with the SP6 tail to create a phage that can attack *Salmonella* and K1 *E. coli*. It should be easy to construct by homologous recombination because of the common sequence upstream of the tail proteins and the common 85 base sequence between the two tail proteins. An alternative is to create a phage that can attack *Salmonella*, K1 *E. coli* and K5 *E. coli* by designing a construct to encode all three proteins. In the case of ΦK1–5, we have evidence that broad host range evolved by the acquisition of a second specific tail protein. Thus, under the theory of modular evolution, in which duplications and rearrangements of regions within tail fiber genes of different phages seem to mediate changes in host specificity, we envision increasing host range even further by designing the acquisition of a third specific tail protein, a fourth specific tail protein, and multiple specific tail proteins.

DEFINITIONS

The term "isolated" requires that a material be removed from its original environment (e.g., the natural environment if it is naturally occurring). For example, a naturally occurring phage present in a natural system is not isolated, but the same phage, separated from some or all of the coexisting materials in the natural system, is isolated.

The term "purified" does not require absolute purity; rather it is intended as a relative definition, with reference to the purity of the material in its natural state. Purification of natural material to at least one order of magnitude, preferably two or three magnitudes, and more preferably four or five orders of magnitude is expressly contemplated.

The term "enriched" means that the concentration of the material is at least about 2, 5, 10, 100, or 1000 times its natural concentration (for example), advantageously 0.01% by weight. Enriched preparations of about 0.5%, 1%, 5%, 10%, and 20% by weight are also contemplated.

Multiple Host Specificity Based On Multiple Different Host Tail Proteins

Phage therapy capitalizes on the ability of phage to lyse bacteria. With the increasing incidence of antibiotic resistant bacteria, there is a need to counteract them. The present invention meets that need by overcoming the additional disadvantage frequently raised to the use of phage, which is their excessively narrow host range.

A prototype bacteriophage has a head and a tail. The head is an icosahedron. The tail consists of a hollow core. The whole apparatus functions as a syringe for injection of phage DNA into the interior of a bacterial cell. The life cycle is that viral genes are expressed, virions are assembled, and cellular lysis releases infectious particles into the medium. In this way, the bacteriophage kill the host pathogen.

One way of evading a host's antibody response is for a bacterium to coat itself with a capsule. A capsule is a network of polymers that is usually composed of polysaccharides, but may be composed of proteins or protein-carbohydrate mixtures, and that resembles host tissue polymers. In *E. coli*, over 70 different polysaccharide or protein K antigens are currently recognized by the World Health Organization.

Bacteriophage carry a tail protein that attaches to a surface structure of a bacterium by which the viral genome enters the infected cell. Some bacteriophage possess a tail protein that contains capsule-degrading enzymatic activity. These enzymes facilitate penetration by bacteriophage of the bacterial cell capsule. In K1 specific bacteriophage, the tail protein is a neuranimidase. In K5 specific bacteriophage, the tail protein is a lyase. In other K specific bacteriophage, the tail protein is another hydrolytic protein.

Phylogenetic classification indicates that gram-negative bacteria form one group of bacteria. *Escherichia, Shigella, Enterobacter* and *Salmonella* are genera of bacteria that are closely related to each other. *Yersinia* and *Vibrio* are the genera next most closely related to the *E. coli* group. *Serratia* and *Klebsiella* are the genera next most closely related to the *E. coli* group. *Campylobacter* is also the genera of Proteobacteria phylum. The genera *Legionella, Pseudomonas,* and *Neisseria* are more distantly related. *Bordetella*'s relationship is unknown. *Helicobacter* is the most distantly related genus in the *E. coli* group of gram-negative bacteria. The gram-positive bacteria form another group, with *Listeria* more closely related to the gram-positive cocci *Staphylococcus* and *Streptococcus, Enterococcus* and *Clostridium,* than to other gram-positive rods. *Corynebacterium* is most closely related to *Mycobacterium*. The spirochetes *Treponema* and *Borrelia* form a third phylogenetic group, while *Chlamydia* is related more distantly to this group. Despite the genetic diversity represented by pathogenic bacteria, similar strategies for overcoming host defenses have evolved in very different types of bacteria. We contemplate using our invention against but not limited to the following pathogenic bacteria presented in the table below.

| Pathogen | Disease | Phage |
|---|---|---|
| *Escherichia* | Hemmorrhagic colitis; thrombocytopenia; hemolytic uremic syndrome | +, ATCC |
| *Shigella* | Dysenteria | +, ATCC |
| *Salmonella* | Typhus | +, ATCC |
| *Enterobacter* | Urinary tract infections | +, ATCC |
| *Yersinia* | Plague | +, ATCC |
| *Vibrio* | Cholera; severe diarrhea, rapid dehydration | +, ATCC |
| *Legionella* | Legionnaires' disease: malaise, myalgia, fever, headache, respiratory illness | — |
| *Pseudomonas* | Opportunistic infections | +, ATCC |
| *Neisseria* | Bacterial meningitis | +, ATCC |
| *Bordetella* | Pertussis (whooping cough) | +, ref[a] |
| *Helicobacter* | Gastritis, peptic ulcers, possibly stomach cancer | +, ref[b] |
| *Listeria* | Listeriosis (meningitis) | +, ATCC |
| *Staphylococcus* | Abscesses, pneumonia, endocarditis, toxic shock | +, ATCC |
| *Streptococcus* | Scarlet fever, rheumatic fever, toxic shock | +, ATCC |
| *Enterococcus* | Urinary tract infections | +, ATCC |
| *Clostridium* | Tetanus | +, ATCC |
| *Corynebacterium* | Diphtheria | +, ATCC |
| *Mycobacterium* | Tuberculosis: cough, weight loss, lung lesions; infection can spread to other organ systems | +, ATCC |
| *Treponema* | Syphilis | +, ref[c] |
| *Borrelia* | Lyme disease: rash, fever, neurological and cardiac abnormalities, arthritis | +, ref[d] |
| *Campylobacter* | Campylobacter enteritis: abdominal pain, diarrhea, fever | +, ATCC |
| *Chlamydia* | Trachoma, genital infections, conjunctivitis, infant pneumonia | +, ref[e] |
| *Haemophilus* | Brazilian purpuric fever: purulent conjunctivitis, fever, vomiting | +, ATCC |
| *Serratia* | Opportunistic infection in neonates | +, ATCC |
| *Kiebsiella* | pneumonia | +, ATCC |

Where:
"+, ATCC" indicates the presence of a corresponding bacteriophage(s) in the ATCC;
"+, ref" indicates that information on the excisting corresponding bacteriophage can be found in the following scientific literature:
ref[a] - Holzmayer TA, et al. 1988 Zentralbl Bakteriol Mikrobiol Hyg [A] 269(2): 147–55; Gol'tsmaier TA, et al. 1987 Zh Mikrobiol Epidemiol Immunobiol 5: 9–13;
ref[b] - Heintschel von Heinegg E, ey al. 1993 J Med Microbiol 38(4): 245–9;
ref[c] - Ritchie AE, et al. 1978 Vet Rec 103(2): 34–5;
ref[d] - Eggers CH, et al. 2000 J Mol Microbiol Biotechnol2(4): 365–73;
ref[e] - Hsia R, et al. 2000 Microbes Infect 2(7): 761–72; Hsia RC, et al. 2000 Microbiology 146 (Pt 7): 1651–60.

In an embodiment of the present invention, a phage has a dual host specificity based on having two different host tail proteins. In another embodiment, a phage has a triple host specificity based on having three different host tail proteins. In a further embodiment, a phage has a quadruple host specificity based on having four different host tail proteins. And so forth, so that in an additional embodiment, a phage has a multiple host specificity based on having multiple different host tail proteins.

In another embodiment of the present invention, a phage having a hydrolytic tail protein has a dual host specificity based on having two different hydrolytic tail proteins. In another embodiment, a phage having a hydrolytic tail protein has a triple host specificity based on having three different hydrolytic tail proteins. In a further embodiment, a phage having a hydrolytic tail protein has a quadruple host specificity based on having four different hydrolytic tail proteins. And so forth, so that in an additional embodiment, a phage having a hydrolytic tail protein has a multiple host specificity based on having multiple different hydrolytic tail proteins.

In another embodiment of the present invention, a phage having a K specific hydrolytic tail protein has a dual host specificity based on having two different K specific hydrolytic tail proteins. In another embodiment, a phage having a K specific hydrolytic tail protein has a triple host specificity based on having three different K specific hydrolytic tail proteins. In a further embodiment, a phage having a K specific hydrolytic tail protein has a quadruple host specificity based on having four different K specific hydrolytic tail proteins. And so forth, so that in an additional embodiment, a phage having a K specific hydrolytic tail protein has a multiple host specificity based on having multiple different K specific hydrolytic tail proteins.

A first example of a phage that has a dual host specificity is ΦK1–5. An example of a phage having a triple host specificity is ΦK1–5 having a third different tail protein. An example of a phage having a quadruple host specificity is ΦK1–5 having a third and fourth different tail protein. And so forth, so that an example of a phage having a multiple host specificity is ΦK1–5 having multiple different host tail proteins.

A second example of a phage that has a dual host specificity is ΦK1E having a second different tail protein, like K1–5. An example of a phage having a triple host specificity is ΦK1E having a second and third different tail protein. An example of a phage having a quadruple host specificity is ΦK1E having a second, third and fourth different tail protein. And so forth, so that an example of a phage having a multiple host specificity is ΦK1E having multiple different host tail proteins.

A third example of a phage that has a dual host specificity is ΦK5 having a second different tail protein, like K1–5. An example of a phage having a triple host specificity is ΦK5 having a second and third different tail protein. An example of a phage having a quadruple host specificity is ΦK5 having a second, third and fourth different tail protein. And so forth, so that an example of a phage having a multiple host specificity is ΦK5 having multiple different host tail proteins.

Another example of a phage that has a multiple host specificity based on having different host tail proteins is a phage that infects *Escherichia* and additionally infects a bacterium selected from the group consisting of *Escherichia, Shigella, Salmonella, Enterobacter, Yersinia, Vibrio, Legionella, Pseudomonas, Neisseria, Bordetella, Helicobacter, Listeria, Staphylococcus, Streptococcus, Enterococcus, Clostridium, Corynebacterium, Mycobacterium, Treponema, Borrelia, Campylobacter, Chlamydia, Haemophilus, Serratia* and *Klebsiella*.

Another example of a phage that has a multiple host specificity based on having different host tail proteins is a phage that infects *Shigella* and additionally infects a bacterium selected from the group consisting of *Escherichia, Shigella, Salmonella, Enterobacter, Yersinia, Vibrio, Legionella, Pseudomonas, Neisseria, Bordetella, Helicobacter, Listeria, Staphylococcus, Streptococcus, Enterococcus, Clostridium, Corynebacterium, Mycobacterium, Treponema, Borrelia, Campylobacter, Chlamydia, Haemophilus, Serratia* and *Klebsiella*.

Another example of a phage that has a multiple host specificity based on having different host tail proteins is a phage that infects *Salmonella* and additionally infects a bacterium selected from the group consisting of *Escherichia, Shigella, Salmonella, Enterobacter, Yersinia, Vibrio, Legionella, Pseudomonas, Neisseria, Bordetella, Helicobacter, Listeria, Staphylococcus, Streptococcus, Enterococcus, Clostridium, Corynebacterium, Mycobacterium, Treponema, Borrelia, Campylobacter, Chlamydia, Haemophilus, Serratia* and *Klebsiella*.

Another example of a phage that has a multiple host specificity based on having different host tail proteins is a phage that infects *Enterobacter* and additionally infects a bacterium selected from the group consisting of *Escherichia, Shigella, Salmonella, Enterobacter, Yersinia, Vibrio, Legionella, Pseudomonas, Neisseria, Bordetella, Helicobacter, Listeria, Staphylococcus, Streptococcus, Enterococcus, Clostridium, Corynebacterium, Mycobacterium, Treponema, Borrelia, Campylobacter, Chiamydia, Haemophilus, Serratia* and *Klebsiella*.

Another example of a phage that has a multiple host specificity based on having different host tail proteins is a phage that infects *Yersinia* and additionally infects a bacterium selected from the group consisting of *Escherichia, Shigella, Salmonella, Enterobacter, Yersinia, Vibrio, Legionella, Pseudomonas, Neisseria, Bordetella, Helicobacter, Listeria, Staphylococcus, Streptococcus, Enterococcus, Clostridium, Corynebacterium, Mycobacterium, Treponema, Borrelia, Campylobacter, Chlamydia, Haemophilus, Serratia* and *Klebsiella*.

Another example of a phage that has a multiple host specificity based on having different host tail proteins is a phage that infects *Vibrio* and additionally infects a bacterium selected from the group consisting of *Escherichia, Shigella, Salmonella, Enterobacter, Yersinia, Vibrio, Legionella, Pseudomonas, Neisseria, Bordetella, Helicobacter, Listeria, Staphylococcus, Streptococcus, Enterococcus, Clostridium, Corynebacterium, Mycobacterium, Treponema, Borrelia, Campylobacter, Chlamydia, Haemophilus, Serratia* and *Klebsiella*.

Another example of a phage that has a multiple host specificity based on having different host tail proteins is a phage that infects *Legionella* and additionally infects a bacterium selected from the group consisting of *Escherichia, Shigella, Salmonella, Enterobacter, Yersinia, Vibrio, Legionella, Pseudomonas, Neisseria, Bordetella, Helicobacter, Listeria, Staphylococcus, Streptococcus, Enterococcus, Clostridium, Corynebacterium, Mycobacterium, Treponema, Borrelia, Campylobacter, Chlamydia, Haemophilus, Serratia* and *Klebsiella*.

Another example of a phage that has a multiple host specificity based on having different host tail proteins is a phage that infects *Pseudomonas* and additionally infects a bacterium selected from the group consisting of *Escherichia, Shigella, Salmonella, Enterobacter, Yersinia, Vibrio, Legionella, Pseudomonas, Neisseria, Bordetella, Helicobacter, Listeria, Staphylococcus, Streptococcus, Enterococcus, Clostridium, Corynebacterium, Mycobacterium, Treponema, Borrelia, Campylobacter, Chlamydia, Haemophilus, Serratia* and *Klebsiella*.

Another example of a phage that has a multiple host specificity based on having different host tail proteins is a phage that infects *Neisseria* and additionally infects a bacterium selected from the group consisting of *Escherichia, Shigella, Salmonella, Enterobacter, Yersinia, Vibrio, Legionella, Pseudomonas, Neisseria, Bordetella, Helicobacter, Listeria, Staphylococcus, Streptococcus, Enterococcus, Clostridium, Corynebacterium, Mycobacterium, Treponema, Borrelia, Campylobacter, Chlamydia, Haemophilus, Serratia* and *Klebsiella*.

Another example of a phage that has a multiple host specificity based on having different host tail proteins is a phage that infects *Bordetella* and additionally infects a bacterium selected from the group consisting of *Escherichia, Shigella, Salmonella, Enterobacter, Yersinia, Vibrio, Legionella, Pseudomonas, Neisseria, Bordetella, Helicobacter, Listeria, Staphylococcus, Streptococcus, Enterococcus, Clostridium, Corynebacterium, Mycobacterium, Treponema, Borrelia, Campylobacter, Chlamydia, Haemophilus, Serratia* and *Klebsiella*.

Another example of a phage that has a multiple host specificity based on having different host tail proteins is a phage that infects *Helicobacter* and additionally infects a bacterium selected from the group consisting of *Escherichia, Shigella, Salmonella, Enterobacter, Yersinia, Vibrio, Legionella, Pseudomonas, Neisseria, Bordetella, Helicobacter, Listeria, Staphylococcus, Streptococcus, Enterococcus, Clostridium, Corynebacterium, Mycobacterium, Treponema, Borrelia, Campylobacter, Chlamydia, Haemophilus, Serratia* and *Klebsiella*.

Another example of a phage that has a multiple host specificity based on having different host tail proteins is a phage that infects *Listeria* and additionally infects a bacterium selected from the group consisting of *Escherichia, Shigella, Salmonella, Enterobacter, Yersinia, Vibrio, Legionella, Pseudomonas, Neisseria, Bordetella, Helicobacter, Listeria, Staphylococcus, Streptococcus, Enterococcus, Clostridium, Corynebacterium, Mycobacterium, Treponema, Borrelia, Campylobacter, Chlamydia, Haemophilus, Serratia and Klebsiella.

Another example of a phage that has a multiple host specificity based on having different host tail proteins is a phage that infects *Staphylococcus* and additionally infects a bacterium selected from the group consisting of *Escherichia, Shigella, Salmonella, Enterobacter, Yersinia, Vibrio, Legionella, Pseudomonas, Neisseria, Bordetella, Helicobacter, Listeria, Staphylococcus, Streptococcus, Enterococcus, Clostridium, Corynebacterium, Mycobacterium, Treponema, Borrelia, Campylobacter, Chlamydia, Haemophilus, Serratia* and *Klebsiella*.

Another example of a phage that has a multiple host specificity based on having different host tail proteins is a phage that infects *Streptococcus* and additionally infects a bacterium selected from the group consisting of *Escherichia, Shigella, Salmonella, Enterobacter, Yersinia, Vibrio, Legionella, Pseudomonas, Neisseria, Bordetella, Helicobacter, Listeria, Staphylococcus, Streptococcus, Enterococcus, Clostridium, Corynebacterium, Mycobacterium, Treponema, Borrelia, Campylobacter, Chlamydia, Haemophilus, Serratia* and *Klebsiella*.

Another example of a phage that has a multiple host specificity based on having different host tail proteins is a phage that infects *Enterococcus* and additionally infects a bacterium selected from the group consisting of *Escherichia, Shigella, Salmonella, Enterobacter, Yersinia, Vibrio, Legionella, Pseudomonas, Neisseria, Bordetella, Helicobacter, Listeria, Staphylococcus, Streptococcus, Enterococcus, Clostridium, Corynebacterium, Mycobacterium, Treponema, Borrelia, Campylobacter, Chlamydia, Haemophilus, Serratia* and *Klebsiella*.

Another example of a phage that has a multiple host specificity based on having different host tail proteins is a phage that infects *Clostridium* and additionally infects a bacterium selected from the group consisting of *Escherichia, Shigella, Salmonella, Enterobacter, Yersinia, Vibrio, Legionella, Pseudomonas, Neisseria, Bordetella, Helicobacter, Listeria, Staphylococcus, Streptococcus, Clostridium, Corynebacterium, Mycobacterium, Treponema, Borrelia, Campylobacter, Chlamydia, Haemophilus, Serratia* and *Klebsiella*.

Another example of a phage that has a multiple host specificity based on having different host tail proteins is a phage that infects *Corynebacterium* and additionally infects a bacterium selected from the group consisting of *Escherichia, Shigella, Salmonella, Enterobacter, Yersinia, Vibrio, Legionella, Pseudomonas, Neisseria, Bordetella, Helicobacter, Listeria, Staphylococcus, Streptococcus, Clostridium, Corynebacterium, Mycobacterium, Treponema, Borrelia, Campylobacter, Chlamydia, Haemophilus, Serratia* and *Klebsiella*.

Another example of a phage that has a multiple host specificity based on having different host tail proteins is a phage that infects *Mycobacterium* and additionally infects a bacterium selected from the group consisting of *Escherichia, Shigella, Salmonella, Enterobacter, Yersinia, Vibrio, Legionella, Pseudomonas, Neisseria, Bordetella, Helicobacter, Listeria, Staphylococcus, Streptococcus, Clostridium, Corynebacterium, Mycobacterium, Treponema, Borrelia, Campylobacter, Chlamydia, Haemophilus, Serratia* and *Klebsiella*.

Another example of a phage that has a multiple host specificity based on having different host tail proteins is a phage that infects *Treponema* and additionally infects a bacterium selected from the group consisting of *Escherichia, Shigella, Salmonella, Enterobacter, Yersinia, Vibrio, Legionella, Pseudomonas, Neisseria, Bordetella, Helicobacter, Listeria, Staphylococcus, Streptococcus, Clostridium, Corynebacterium, Mycobacterium, Treponema, Borrelia, Campylobacter, Chlamydia, Haemophilus, Serratia* and *Klebsiella*.

Another example of a phage that has a multiple host specificity based on having different host tail proteins is a phage that infects *Borrelia* and additionally infects a bacterium selected from the group consisting of *Escherichia, Shigella, Salmonella, Enterobacter, Yersinia, Vibrio, Legionella, Pseudomonas, Neisseria, Bordetella, Helicobacter, Listeria, Staphylococcus, Streptococcus, Clostridium, Corynebacterium, Mycobacterium, Treponema, Borrelia, Campylobacter, Chlamydia, Haemophilus, Serratia* and *Klebsiella*.

Another example of a phage that has a multiple host specificity based on having different host tail proteins is a phage that infects *Campylobacter* and additionally infects a bacterium selected from the group consisting of *Escherichia, Shigella, Salmonella, Enterobacter, Yersinia, Vibrio, Legionella, Pseudomonas, Neisseria, Bordetella, Helicobacter, Listeria, Staphylococcus, Streptococcus, Clostridium, Corynebacterium, Mycobacterium, Treponema, Borrelia, Campylobacter, Chlamydia, Haemophilus, Serratia* and *Klebsiella*.

Another example of a phage that has a multiple host specificity based on having different host tail proteins is a phage that infects *Chlamydia* and additionally infects a bacterium selected from the group consisting of *Escherichia, Shigella, Salmonella, Enterobacter, Yersinia, Vibrio, Legionella, Pseudomonas, Neisseria, Bordetella, Helicobacter, Listeria, Staphylococcus, Streptococcus, Clostridium, Corynebacterium, Mycobacterium, Treponema, Borrelia, Campylobacter, Chlamydia, Haemophilus, Serratia* and *Klebsiella*.

Another example of a phage that has a multiple host specificity based on having different host tail proteins is a phage that infects *Haemophilus* and additionally infects a bacterium selected from the group consisting of *Escherichia, Shigella, Salmonella, Enterobacter, Yersinia, Vibrio, Legionella, Pseudomonas, Neisseria, Bordetella, Helicobacter, Listeria, Staphylococcus, Streptococcus, Clostridium, Corynebacterium, Mycobacterium, Treponema, Borrelia, Campylobacter, Chlamydia, Haemophilus, Serratia* and *Klebsiella*.

Another example of a phage that has a multiple host specificity based on having different host tail proteins is a phage that infects *Serratia* and additionally infects a bacterium selected from the group consisting of *Escherichia, Shigella, Salmonella, Enterobacter, Yersinia, Vibrio, Legionella, Pseudomonas, Neisseria, Bordetella, Helicobacter, Listeria, Staphylococcus, Streptococcus, Clostridium, Corynebacterium, Mycobacterium, Treponema, Borrelia, Campylobacter, Chlamydia, Haemophilus, Serratia* and *Klebsiella*.

Another example of a phage that has a multiple host specificity based on having different host tail proteins is a phage that infects *Klebsiella* and additionally infects a bacterium selected from the group consisting of *Escherichia, Shigella, Salmonella, Enterobacter, Yersinia, Vibrio, Legionella, Pseudomonas, Neisseria, Bordetella, Helicobacter, Listeria, Staphylococcus, Streptococcus, Clostridium, Corynebacterium, Mycobacterium, Treponema, Borrelia, Campylobacter, Chlamydia, Haemophilus, Serratia* and *Klebsiella*.

Host Range of Phage to Include Bacterial Cells Requiring Co-factors

In another embodiment of the present invention, a phage that has a multiple host specificity based on having multiple different host tail proteins additionally has a gene encoding a co-factor that permits it to grow in other types of bacteria. Having the proper tail proteins is necessary for a phage to infect a strain of bacteria, as illustrated by the present experiments. For example, a phage having different host tail proteins is capable of infecting multiple hosts where the host expresses at least one of these host tail proteins. Nevertheless, additional factors may be necessary for a phage to infect other strains of bacteria. The present invention provides these phage where co-factors may also be needed to increase their host range.

For example the *E. coli* phage lambda does not generally infect Salmonella. *E. coli* phage lambda requires a functional *E. coil* Nus A gene for lambda promoted transcription/anti-termination of DNA→RNA to permit the virus to replicate and function. As the bacteria *Salmonella* does not have the *E. coli* Nus A gene, lambda cannot grow in *Salmonella*. When the *E. coli* Nus A gene is cloned into the lambda genome, this virus can then infect certain *Salmonella* stains. In a confirmatory experiment, the *E. coli* genome was cut into fragments with restriction enzymes and the fragments cloned into a lambda library. When these lambda phage were plated on *Salmonella*, only those containing *E. coli* Nus A gene grew. Thus, lambda carrying the *E. coli* Nus A gene provides one example of how the host range of a phage can be expanded.

In another example of a phage that does not generally infect another type of bacteria, the gene that permits the virus to replicate and function in the bacteria may be known. If known, the gene can be cloned into the viral genome so that this virus can then infect other types of bacteria. If unknown, the gene can be identified, for example, by cutting the bacterial genome into fragments with restriction enzymes and then cloning the fragments into a library of that virus. When these phage are plated on the bacteria, only those containing the gene will grow. Thus, the gene that permits the virus to replicate and function in the bacteria can be identified. Once the gene is known, virus can be engineered to carry the gene. Thus, the host range of the phage can be expanded even when co-factors are necessary to grow in other types of bacteria.

Host Range of Phage to Include Mammalian Cells

In another embodiment of the present invention, a phage has mammalian host specificity based on incorporating the gene for a cell surface-receptor ligand into the phage genome such that it is expressed on the tail of the phage, thus faciliating receptor mediated endocytosis. Poul et al., J Mol Biol 1999, 288:203 and Larocca et al., FASEB J 1999, 13:727 describe gene delivery to mammalian cells by bacteriophage expressing cell surface-receptor ligands as genetic fusions with phage coat proteins or presenting cell surface-receptor ligands on the coats of phage, with the goal being the development of gene therapy vectors. The present invention envisions substituting phage tail proteins.

A cell surface-receptor ligand is genetically fused to a phage tail protein or otherwise presented on the tails of phage. Nucleotide sequences encoding ligand-phage fusions or cell surface-receptor ligands themselves may also be modified by insertion of mammalian reporter genes to test for binding, internalization, and expression. Ultimately, the mammalian reporter gene is replaced by a therapeutic nucleotide sequence.

The therapeutic nucleotide sequence encodes a factor having a therapeutic effect. In alternative embodiments, a factor is a protein cytocide, an antisense, a ribozyme, a dominant negative mutant, or a therapeutic protein (e.g., a growth factor, a hormone, a cytokine, a receptor, or a ligand). An example of receptor-mediated gene delivery using bacteriophage vectors displaying ligands as genetic fusions with phage coat proteins or presenting cell surface-receptor ligands on the coats of phage is set forth in U.S. Pat. No. 6,054,312 to Larocca et al.

Methods of Making

In a different embodiment, the acquisition of new tail genes occurs by recombination in nature. In an alternative embodiment, the acquisition of new tail genes is generated by technology in the laboratory. Thus, the phage may be developed by selection or engineering.

Phage that have multiple specificities may be selected by assays to determine the host range of phages, such as plaque assays.

Alternatively, phage that have multiple specificities may be engineered by cloning the gene for a tail protein into a plasmid vector system and then incorporating this configuration into the phage of interest by an in vivo generalized recombination system in the host bacteria for the phage of interest; or by cloning the gene for a first tail protein into a plasmid vector system, and then cloning the gene for a second tail protein into this carrying vector by in-frame fusion at the 3'- or 5'- end of the gene for the first tail protein, and then incorporating this configuration into the phage of interest by an in vivo generalized recombination system in the host bacteria for the phage of interest; or by cloning the gene for a first tail protein into a plasmid vector system, and then cloning the gene for a second tail protein into this carrying vector by in-frame fusion at the 3'- or 5'- end of the gene for the first tail protein, and then cloning the gene for a third tail protein into this carrying vector by in-frame fusion at the 3'- or 5'- end of the genes for the first and second tail proteins, and so forth, and then incorporating this configuration into the phage of interest by an in vivo generalized recombination system in the host bacteria for the phage of interest.

Methods of Using, Formulations, and Administration

The present invention can be applied across the spectrum of bacterial diseases, by selecting or engineering phages, so that phages are developed that are specific for more than one bacterial strain of interest. In that way, a full array of polyvalent bacteriophages is developed for virtually all the bacterial pathogens for man, his pets, livestock and zoo animals (whether mammal, avian, or pisciculture). Phage therapy will then be available:

1) as an adjunct to or as a replacement for those antibiotics and/or chemotherapeutic drugs that are no longer functioning in a bacteriostatic or bactericidal manner due to the development of multi-drug resistance;

2) as a treatment for those patients who are allergic to the antibiotics and/or chemotherapeutic drugs that would otherwise be indicated; and 3) as a treatment that has fewer side effects than many of the antibiotics and/or chemotherapeutic drugs that would otherwise be indicated for a given infection.

Another embodiment of the present invention is the development of methods to treat bacterial infections in animals through phage therapy with the polyvalent bacteriophages described above. Hundreds of bacteriophages and the bacterial species they infect are known in the art. The present invention can be utilized to develop polyvalent bacteriophages that can be used to treat any and all infections caused by their host bacteria.

While it is contemplated that the present invention can be used to treat any bacterial infection in an animal and human, it is particularly contemplated that the methods described herein will be very useful as a therapy (adjunctive or stand-alone) in infections caused by drug-resistant bacteria. Experts report (See e.g. Gibbons, A., "Exploring New Strategies to Fight Drug-Resistant Microbes, Science, 21 Aug. 1993, pp. 1036–38) that at the present time, the drug-resistant bacterial species and strains listed below represent the greatest threat to mankind:

1. All of the clinically important members of the family *Enterobacteriaceae*, most notably but not limited to the following:

a) All the clinically important strains of *Escherichia*, most notably *E. coli*. One among a number of candidate wild-type phages against these particular pathogens that could be used as a starting point for the genetic engineering of the present invention would be θK1–5 having ATCC Accession No. # PTA-3495. (Note: For purposes of brevity, in all the following examples of pathogens, the corresponding wild-type phage will be indicated by the following phraseology: "Example of corresponding phage: _____".)

b) All the clinically important strains of *Klebsiella*, most notably *K. pneumoniae* (Example of corresponding phage: ATCC phage #23356-B1).

c) All the clinically important strains of *Shigella*, most notably *S. dysenteriae* (Example of corresponding phage: ATCC phage #11456a-B1).

d) All the clinically important strains of *Salmonella*, including *S. abortus-equi* (Example of corresponding phage: ATCC phage #9842-B1), *S. typhi* (Example of corresponding phage: ATCC phage #19937-B1) *S. typhimurium* (Example of corresponding phage: ATCC phage #19585-B1), *S. newport* (Example of corresponding phage: ATCC phage #27869-B1), *S. paratyphi*-A (Example of corresponding phage: ATCC phage #12176-B1), *S. paratyphi*-B (Example of corresponding phage: ATCC phage #19940-B1), *S. potsdam* (Example of corresponding phage: ATCC phage #25957-B2), and *S. pollurum* (Example of corresponding phage: ATCC phage #19945-B1).

e) All the clinically important strains of *Serratia*, most notably *S. marcescens* (Example of corresponding phage: ATCC phage #14764-B1).

f) All the clinically important strains of *Yersinia*, most notably *Y. pestis* (Example of corresponding phage: ATCC phage #11953-B1).

g) All the clinically important strains of *Enterobacter*, most notably *E. cloacae* (Example of corresponding phage: ATCC phage #23355-B1).

2. All the clinically important *Enterococci*, most notably *E. faecalis* (Example of corresponding phage: ATCC phage #19948-B1) and *E. faecium* (Example of corresponding phage: ATCC phage #19953-B1).

3. All the clinically important *Haemophilus* strains, most notably *H. influenzae* (a corresponding phage is not available from ATCC for this pathogen, but several can be obtained from WHO or other labs that make them available publicly).

4. All the clinically important Mycobacteria, most notably *M. tuberculosis* (Example of corresponding phage: ATCC phage #25618-B1), *M. avium-intracellulare, M. bovis*, and *M. leprae*. (Corresponding phages for these pathogens are available commercially from WHO, via The National Institute of Public Healthy & Environmental Protection, Bilthoven, The Netherlands).

5. *Neisseria gonorrhoeae* and *N. meningitidis* (Corresponding phage for both can be obtained publicly from WHO or other sources).

6. All the clinically important *Pseudomonads*, most notably *P. aeuruginosa* (Example of corresponding phage: ATCC phage #14203-B1).

7. All the clinically important *Staphylococci*, most notably *S. aureus* (Example of corresponding phage: ATCC phage #27690-B1) and *S. epidermidis* (Corresponding phage are available publicly through the WHO, via the Colindale Institute in London).

8. All the clinically important *Streptococci*, most notably *S. pneumoniae* (Corresponding phage can be obtained publicly from WHO or other sources).

9. *Vibrio cholera* (Example of corresponding phage: ATCC phage #14100-B1).

There are additional bacterial pathogens too numerous to mention that, while not currently in the state of antibiotic-resistance crisis, nevertheless make excellent candidates for treatment with polyvalent bacteriophages in accordance with the present invention. Thus, all bacterial infections caused by bacteria for which there is a corresponding phage can be treated using the present invention.

Any phage strain capable of doing direct or indirect harm to a bacteria (or other pathogen) is contemplated as useful in the present invention. Thus, phages that are lytic, phages that are lysogenic but can later become lytic, and nonlytic phages that can deliver a product that will be harmful to the bacteria are all useful in the present invention.

The animals to be treated by the methods of the present invention include but are not limited to man, his domestic pets, livestock, pisciculture, and the animals in zoos and aquatic parks.

The polyvalent bacteriophages of the present invention can be used as a stand-alone therapy or as an adjunctive therapy for the treatment of bacterial infections. Numerous antimicrobial agents (including antibiotics and chemotherapeutic agents) are known in the art, which would be useful in combination with polyvalent bacteriophages for treating bacterial infections. Examples of suitable antimicrobial agents and the bacterial infections that can be treated with the specified antimicrobial agents are listed below. However, the present invention is not limited to the antimicrobial agents listed below as one skilled in the art could easily determine other antimicrobial agents useful in combination with polyvalent bacteriophages.

| Pathogen | Antimicrobial or antimicrobial group |
|---|---|
| *E. coli* | |
| Uncomplicated urinary tract infection | trimethoprim-sulfamethoxazole (abbrev. TMO-SMO), or ampicillin; 1st generation cephalosporins, ciprofloxacin |

-continued

| Pathogen | Antimicrobial or antimicrobial group |
|---|---|
| Systemic infection | ampicillin, or a 3rd generation cephalosporin; aminoglycosides, aztreonam, or a penicillin + a pencillinase inhibitor |
| *Klebsiella pneumoniae* | 1st generation cephalosporins; 3rd gener. cephalosporins, cefotaxime, moxalactam, amikacin, chloramphenicol |
| *Shigella* (various) | ciprofloxacin; TMO-SMO, ampicillin, chloramphenicol |
| *Salmonella:* | |
| *s. typhi* | chloramphenicol; ampicillin or TMO-SMO |
| Non-typhi species | ampicillin; chloramphenicol, TMO-SMO, ciprofloxacin |
| *Yersinia pestis* | streptomycin; tetracycline, chloramphenicol |
| *Enterobacter cloacoe* | 3rd generation cephalosporins, gentamicin, or tobramycin; carbenicillin, amikacin, ztreonam, imipenem |
| *Hemophilus influenzae:* | |
| Meningitis | chloramphenicol or 3rd generation cephalosporins; ampicillin |
| Other *H. infl.* Infections | ampicillin; TMO-SMO, cefaclor, cefuroxime, ciprofloxacin |
| *Mycobacterium tuberculosis* and *M. avium-intracellulare* | isoniazid (INH) + rifampin or rifabutin, the above given along with pyrazinamide +/or ethambutol |
| *Neisseria:* | |
| *N. meningitidis* | penicillin G; chloramphenicol, or a sulfonamide |
| *N. gonorrhoeae:* | |
| Penicillin-sensitive | penicillin G; spectinomycin, ceftriaxone |
| Penicilin-resistant | ceftriaxone; spectinomycin, cefuroxime or cefoxitin, ciprofloxacin |
| *Pseudomonas aeruginosa* | tobramycin or gentamycin (+/− carbenicillin, aminoglycosides); amikacin, ceftazidime, aztreonam, imipenem |
| *Staph aureus* | |
| non-penicillinase producing | penicillin G; 1st generation cephalosporins, vancomycin, imipenem, erythromycin |
| Penicillinase producing | a penicillinase-resisting penicillin; 1st generation cephalosporins, vanco-mycin, imipenem, erythromycin |
| *Streptococcus pneumoniae* | penicillin G; 1st generation cephalosporins, erythromycin, chloramphenicol |
| *Vibrio cholera* | tetracycline; TMO-SMO |

In another embodiment of the present invention, the polyvalent bacteriophages of the invention are provided as compositions useful in the treatment and prevention of various bacterial infections, such as diarrhea, dysentery, hemolytic uremic syndrome, bladder infection, kidney infection, urinary tract infection, septicemia, pneumonia, and meningitis, and other various diseases, syndromes, and disorders.

The polyvalent bacteriophage of the invention can be used for the treatment or prevention of *Hemophilus influenza*, *Pseudomonas*, *Streptococcus pneumoniae*, *Streptococcus fasciae*, *Streptococcus* group B, *Listeria*, *Salmonella*, *E. coli*, *Campylobacter*, and other bacteria, and any combination thereof. For example, if there is a bacterial infection of the upper respiratory tract, the infection can be prophylactically or therapeutically treated with a composition comprising at least one polyvalent bacteriophage specific for that bacteria, and a carrier for delivering the polyvalent bacteriophage to a mouth, throat, or nasal passage. If an individual has been exposed to someone with the upper respiratory disorder, the polyvalent bacteriophage will reside in the mucosal lining and prevent any colonization of the infecting bacteria.

Two examples of bacteria which infect the upper respiratory system are *Streptococcus pneumoniae* and *Hemophilus influenzae*. In recent years, there has been an increase in the number of people, particularly children and the elderly, that are infected or are carriers of penicillin resistant *Streptococcus pneumoniae* and *Hemophilus*. While these bacteria are normally harmless residents of the host, they are opportunistic organisms that are able to cause infections when the resistance of the host has been compromised. By eliminating or reducing the number of these organisms in the upper respiratory tract, there will be a commensurate reduction in the number of infections by these bacteria.

The *Hemophilus* bacteria is infected by bacteriophage HP1 (a member of the P2-like phage family with strong similarities to coliphages P2 and 186, and some similarity to the retronphage Ec67), which produces a lytic enzyme capable of lysing the bacteria. *Streptococcus pneumoniae* is infected with the Pa1 bacteriophage, which produces a lytic enzyme identified as an N-acetyl-muramoyl-L-alanine amidase. The pharmaceutical composition of the invention can contain either one polyvalent bacteriophage that recognizes these two bacteria, and may contain other polyvalent bacteriophage for other bacteria. The composition which may be used for the prophylactic and therapeutic treatment of a strep infection includes the polyvalent bacteriophage and a means of application, (such as a carrier system or an oral delivery mode), to the mucosal lining of the oral and nasal cavity, such that the polyvalent bacteriophage is put in the carrier system or oral delivery mode to reach the mucosal lining. Another infection which can be treated prophylactically is *Streptococcus* group A, which can produce what is commonly known as "strep" throat. Group A *Streptococci* are infected with a C1 bacteriophage, which produces a lysing enzyme specific for the lysing of *Streptococcus* group A.

Another use of a polyvalent bacteriophage of the invention is for the treatment of bacterial infections of the digestive tract. The method for treating a bacterial infection of the digestive tract comprises treating the bacterial infection with composition comprising an effective amount of at least one polyvalent bacteriophage specific for the bacteria, and a carrier for delivering said polyvalent bacteriophage to the digestive tract. In a preferred embodiment of the invention, the bacterial infections being treated are being caused by gram negative bacteria selected from the group consisting of *Listeria, Salmonella, E. coli,* and *Campylobacter*. However, this method and composition will effectively treat other bacteria, when the appropriate polyvalent bacteriophage is used.

Another composition and use of the polyvalent bacteriophage of the invention is for the therapeutic or prophylactic treatment of bacterial infections of burns and wounds of the skin. The composition comprises an effective amount of at least one polyvalent bacteriophage specific for the bacteria and a carrier for delivering at least one polyvalent bacteriophage to the wounded skin. The polyvalent bacteriophage may be applied to a bandage either directly or in one or another carrier. The bandages may be sold damp or dry, wherein the polyvalent bacteriophage is in a lyophilized form on the bandage. This method of application is most effective for the treatment of burns. In some embodiments of the invention, polyvalent bacteriophage for Pseudomonas, Staphylococcus, and *Streptococcus*, jointly or individually, may be incorporated into one or another carrier, or into a bandage to be used on burn patients.

Yet another use of polyvalent bacteriophages is for the bacterial infections caused by K1 and/or K5 strains of *E. coli*. These bacteria are involved in a variety of infections, the most common are urinary tract infections (UTI). The polyvalent bacteriophage of the present invention would be applied directly to the site of infection, in the case of UTI this would mean to deliver the phage to the bladder through a catheter.

In the case of septicemias caused by K1 *E coli*, the polyvalent phage of the present invention could be injected directly into the circulatory system or intraperitoneally.

In case of meningitis caused by *E. coli*, the polyvalent phage of the present invention will be delivered to the cerebro-spinal fluid or directly applied to the brain or meninges.

Yet another use of the polyvalent bacteriophages of the invention is for the prophylactic or therapeutic treatment of vaginal infections. This treatment comprises treating the vaginal infection with an effective amount of at least one polyvalent bacteriophage specific for that bacteria, wherein that polyvalent bacteriophage is incorporated in a carrier to be placed in a vagina. The preferred carrier is a tampon, or vaginal douche. A pad may also be used as a carrier, although it is not as effective. While any number of bacteria could be treated using this composition and method, it is believed that the most optimum use of this treatment composition and method would be for the treatment of an *E. coli* and *Streptococcus* B infection. Vaginal infections caused by Group B *Streptococcus* can cause neonatal meningitis resulting in brain damage and premature death. Polyvalent bacteriophage incorporated into tampons specific for group B Strep would eliminate the group B organisms without disturbing normal flora so that women would not be overcome by yeast infections post antibiotic therapy. The use of the polyvalent bacteriophage in the vagina would best provide a prophylactic effect, although therapeutic use would also be advisable.

Another use of the invention is for the prophylactic and therapeutic treatment of eye infections. The method of treatment comprises administering eye drops which comprise an effective amount of at least one polyvalent bacteriophage specific for the bacteria and a carrier capable of being safely applied to an eye, with the carrier containing the polyvalent bacteriophage. In some embodiments of the invention, the bacteria being treated is *Hemophilus* or *Staphylococcus*. The eye drops are in the form of an isotonic solution.

Polyvalent bacteriophage can also be used to fight dental caries. Specifically, a polyvalent bacteriophage specific for *Streptococcus mutans* may be incorporated in a toothpaste or oral wash. Similarly, this polyvalent bacteriophage may also be incorporated into a chewing gum or lozenge. Any other carrier can be used that allows for the exposure of the mouth, gums, and teeth to the polyvalent bacteriophage.

The routes of administration include but are not limited to oral, aerosol, intranasal, intravenous, intramuscular, intraperitoneal, intrathecal, vaginal, rectal, topical, lumbar puncture, and direct application to the brain or meninges. Pharmaceutically acceptable excipients which can be used as a vehicle for the delivery of the phage will be apparent to those skilled in the art. For example, the free phage could be in lyophilized form and be dissolved just prior to administration by IV injection. The dosage of administration is contemplated to be in the range of about $10^6$ to about $10^{13}$ pfu/per kg/per day, and preferably about $10^{12}$ pfu/per kg/per day. The phage are administered until successful elimination of the pathogenic bacteria is achieved.

With respect to the aerosol administration to the lungs, the polyvalent bacteriophage is incorporated into an aerosol formulation specifically designed for administration to the lungs by inhalation. Many such aerosols are known in the art, and the present invention is not limited to any particular formulation. An example of such an aerosol is the Proventil™ inhaler manufactured by Schering-Plough, the propellant of which contains trichloromonofluoromethane, dichlorodifluoromethane and oleic acid. The concentrations of the propellant ingredients and emulsifiers are adjusted if necessary based on the phage being used in the treatment. The number of phage to be administered per aerosol treatment will be in the range of $10^6$ to $10^{13}$ pfu, and preferably $10^{12}$ pfu.

Isolation and Characterization of ΦK1–5

ΦK1–5 was isolated using *E. coli* ATCC 23506 (K5) as a host. Electron micrographs show that ΦK1–5 is morphologically similar to the *Podoviridae* family, which includes coliphages T7, T3, and *Salmonella* phages SP6 and P22. The phage particle consists of an icosohedral head of about 60 nm in diameter with a small tuft of short tail fibers (FIG. 1). ΦK1–5 is highly lytic. When phage were added to a logarithmic culture of a susceptible host at an multiplicity of infection (moi) of 1:1, lysis occurs in 15–20 min. Burst size was determined by a one step growth curve and found to be to be about 110. ΦK1–5 plaques are clear and large, about 4.0–5.0 mm in diameter with a halo of about 12.0–15.0 mm in diameter on LB agar plates. The plaques reached a limit in size after 24 hours. In contrast, T7 plaques, can continue to grow for several days (38). DNA was isolated from cesium chloride density gradient purified phage by phenol extraction. Digestion of the DNA with several restriction enzymes indicated that it is double stranded, with an estimated size of 40 kb.

Extended Host Range of ΦK1–5

The host range of ΦK1–5 was compared to that of ΦK1E (K1 antigen specific) and ΦK5 (K5 antigen specific). *E. coli* strains ATCC 23506 and ATCC 23508 possess the K5 polysaccharide capsule, and strains ATCC 23503 and ATCC 23511 possess the K1 capsule. Also tested was a set of K5 strains collected by Ian Roberts from the University of Manchester and a set of K1 isolates collected by Richard Silver from the University of Rochester (Table 1). ΦK1–5 is able to infect and grow on all of the K1 and K5 strains, ΦK1E only grows on the K1 strains and ΦK5 only grows on the K5 strains. ΦK1E, ΦK5, and ΦK1–5 were also tested for growth on the following ATCC strains: 23502 (K4), 23504 (K8), 23505 (K9),23507 (K10), 23509 (K11), 23510 (K14), 23515 (K17), 23516 (K20), 23517 (K13), 23518 (K18), 19110 (K7), 19138 (K2) and 31616 (K35). No phage growth by ΦK1–5, ΦK1E or ΦK5 was seen on any of these strains.

TABLE 1

Host ranges of phages ΦK1E, ΦK5, ΦK1-5, ΦK1-5$_{(K1^-)}$, and ΦK1-5$_{(K5^-)}$[a]

| E. coli strain | K antigen | ΦK1-5 | ΦK1E | ΦK5 | ΦK1-5$_{(K1^-)}$ | ΦK1-5$_{(K5^-)}$ |
|---|---|---|---|---|---|---|
| ATTCC 23503 | K1 | + | + | − | − | + |
| ATCC 23511 | K1 | + | + | − | − | + |
| RS164 | K1 | + | − | − | − | + |
| RS166 | K1 | + | + | − | − | + |
| RS167 | K1 | + | + | − | − | + |
| RS168 | K1 | + | − | − | − | + |
| RS176 | K1 | + | + | − | − | + |
| RS179 | K1 | + | + | − | − | + |
| RS180 | K1 | + | − | − | − | + |
| RS188 | K1 | + | + | − | − | + |
| RS203 | K1 | + | + | − | − | + |
| RS215 | K1 | + | − | − | − | + |
| RS218 | K1 | + | + | − | − | + |
| RS228 | K1 | + | + | − | − | + |
| ATCC 23506 | K5 | + | − | + | + | − |
| ATCC 23508 | K5 | + | − | + | + | − |
| 20026 | K5 | + | − | + | + | − |
| 21195 | K5 | + | − | + | + | − |
| 21386 | K5 | + | − | + | + | − |
| 21786 | K5 | + | − | + | + | − |
| 21795 | K5 | + | − | + | + | − |
| 21831 | K5 | + | − | + | + | − |
| 21832 | K5 | + | − | + | + | − |
| 21834 | K5 | + | − | + | + | − |
| 21835 | K5 | + | − | + | + | − |

[a]Plaque assays were done to determine host range of the phages against a collection of K1 and K5 strains of E. coli. ΦK1E only grows on K1 strains, ΦK5 only grows on ΦK5 strains and ΦK1-5 grows on both. ΦK1-5$_{(K1^-)}$ and ΦK1-5$_{(K5^-)}$ are mutants of ΦK1-5 defective in growth on K1 and K5 strains, respectively.

Because of the promoter sequence similarity between ΦK1–5 and SP6, we tested if ΦK1–5 could grow on *Salmonella typhimurium* strain LT2 (the host for SP6) and if SP6 could grow on any of the *E. coli* isolates sensitive to ΦK1–5. SP6 did not grow on any of the *E. coli* strains, and likewise ΦK1–5 did not grow on *Salmonella typhymurium*.

ΦK1–5 Encodes Two Tail Genes

ΦK1E and ΦK5 share a region of sequence similarity upstream of the tail proteins (including the SP6-like promoter, 3). Since ΦK1–5 had structural, biological and host similarities to these two phages, we speculated that all three may be closely related to and share this upstream sequence similarity. We designed a primer based on the sequence of this region in ΦK1E and ΦK5 to determine the sequence downstream of the promoter. When ΦK1–5 DNA was used as a template, the primer did hybridize, and we were able to generate sequence. We continued sequencing downstream by primer walking. The sequence immediately downstream of the promoter was very similar to ΦK5, and encoded an open reading frame with a high degree of sequence similarity (>92% amino acid identity) to that of ΦK5 tail protein. Continued sequencing downstream revealed a second open reading frame that is nearly identical (>97% amino acid identity) to the endosialidase protein of ΦK1E. An intergenic region of 85 base pairs lies between the termination codon of the lyase gene and the start codon of the endosialidase gene. This region is also present in ΦK5, immediately following the K5 lyase gene, and also in ΦK1E, immediately upstream of the endosialidase gene and immediately downstream of a 111 amino acid open reading frame (ORF$_L$, 6). No recognizable promoter was found in this region, but there are two strong regions of symmetry, which may act as a Rho-independent transcriptional terminator. Sequence was determined 598 base pairs downstream of the termination codon of the endosialidase gene, at which point the end of the DNA molecule was reached. No open reading frames were found in this area.

The sequence 500 base pairs upstream of the K5 lyase gene in ΦK1–5 was also determined. Like in the other phages, an SP6-like promoter is present and is probably required for transcription of the tail genes. The upstream sequence shares a high degree (>90%) of identity to that of the analogous region in ΦK5 and ΦK1E.

We also sequenced downstream of the endosialidase gene of ΦK1E; 718 base pairs downstream from the endosialidase termination codon we reached the end of the DNA molecule. There is little sequence similarity between this region and the analogous region in ΦK1–5.

Each ΦK1–5 Virion Contains Both Tail Proteins

We addressed the question of whether ΦK1–5 particles contain both tail fiber proteins, or if two populations of particles (one containing the K5 lyase and the other containing the endosialidase) were produced after infection. We made a phage preparation using ATCC 23506 (K5) as a host and determined its titer on ATCC 23506 (K5) and ATCC 23503 (K1) (Table 2). A sample of the phage was then incubated with ATCC 23506 for 5 min, which is long enough for phage to attach and possibly inject the DNA but not long enough for production of new phage particles. The MOI was 1/100 phage particle/bacteria. The mixture was then rapidly filtered. Phage particles that had attached to the cells would be eliminated from the filtrate. The filtrate was then titered on both the K1 and K5 strains. If the phage preparation was initially a mixture of two populations, then only those displaying the K5 lyase would attach and be eliminated. The remaining phage would be mainly those that contained the K1 specific endosialidase, and therefore the titer would be higher on the K1 *E. coli* strains than on the K5 strain. On the other hand, if each of the phage particles contained both tail proteins, titers of the phage remaining in the filtrate would be the same on the two strains, i.e., levels of the K5 lyase containing phages would not be selectively reduced. We found the latter to be the case and concluded that each virion has both the K1 endosialidase and the K5 lyase. Similar results were seen in the converse experiment in which the 5-min incubation was performed using the K1 *E. coli* strain (Table 2). As controls we performed the experiments with both ΦK1E and ΦK5, using both strains for the incubation. ΦK1E titers were reduced 99% by pre-incubation with the K1 strain but not with the K5 strain, and ΦK5 titers were similarly reduced after pre-incubation with the K5 strain but not with the K1 strain.

TABLE 2

Preincubation experiments to show that all ΦK1-5 particles contain both tail proteins[a]

| Phage | Titer |
|---|---|
| ΦK1-5 | |
| Preincubated with 23506 | $5.2 \times 10^8$ |
| Titered on 23506 after preincubation | $3.1 \times 10^6$ |
| Titered on 23503 after preincubation | $3.7 \times 10^6$ |

TABLE 2-continued

Preincubation experiments to show that all ΦK1-5 particles contain both tail proteins[a]

| Phage | Titer |
|---|---|
| Preincubated with 23503 | $5.2 \times 10^8$ |
| Titered on 23506 after preincubation | $6.8 \times 10^6$ |
| Titered on 23503 after preincubation | $6.4 \times 10^6$ |
| ΦK5 | |
| Preincubated with 23506 | $4.0 \times 10^8$ |
| Titered on 23506 after preincubation | $8.5 \times 10^5$ |
| Preincubated with 23503 | $4.0 \times 10^8$ |
| Titered on 23506 after preincubation | $3.3 \times 10^8$ |
| ΦK1E | |
| Preincubated with 23506 | $7.7 \times 10^8$ |
| Titered on 23503 after preincubation | $6.8 \times 10^8$ |
| Preincubation with 23503 | $7.7 \times 10^8$ |
| Titered on 23503 after preincubation | $3.0 \times 10^6$ |

[a]Preincubation of ΦK1-5 with either ATCC 23503 (K1) or ATCC 23506 (K5) for 5 min results in roughly 100-fold loss of phage particles when titered on either strain. If the phage preparation consisted of two populations that each contained just one tail protein, then titers after the incubation would be reduced only on the strain that was used in the preincubation. ΦK5 titers are reduced by preincubation with a permissive host (23506) but not with a nonpermissive host (23503). ΦK1E titers are also reduced only by preincubation on a permissive host (23503) and not a nonpermissive host (23506).

ΦK1–5 Mutants Defective in Growth on Either K1 or K5 *E. coli*

A mixed lawn of K1 and K5 strains of *E. coli* was used to screen for ΦK1–5 mutants defective in growth on one or the other host strains. ΦK1–5 forms clear plaques on a mixed lawn of K1 and K5 *E. coli*; mutants in either tail would result in turbid plaques due to growth of the nonpermissive host. Phage were treated with the mutagen hydroxylamine and plated on a double lawn. Turbid plaques were identified, picked, and purified by multiple plaque isolations on the double lawn. These were then screened by separately testing for growth on each strain. Of eight isolates purified, three were unable to plaque on the K5 strain but could plaque on the K1 strain. One of these, $\Phi K1-5_{(K5-)}$, was screened for growth against the entire host collection and found to be unable to replicate on any of the K5 strains but was able to grow on all of the K1 strains (Table 1). Five of the isolates could still replicate on both K1 and K5 strains but gave a turbid plaque morphology on the on the K5 strains.

None of the mutants isolated in this way were defective in growth on K1 strains, so we devised a selection/amplification scheme to enrich for those that can replicate on K5 but not K1 hosts. Mutagenized phage were amplified on a K5 strain, filtered to remove bacterial debris, then used to infect a logarithmically growing K1 strain for 5 minutes. This mixture was rapidly filtered before phage burst could occur. Phage able to grow on K1 strain would attach to the cells and be eliminated from the filtrate. The sample was then reamplified on the K5 strain and the cycle was repeated eight times. This strongly selects for phage that can replicate on K5 hosts but not K1 hosts. Titers of the filtrate were 200 fold higher on the K5 strain than on the K1 strain. Several were picked and purified by multiple rounds of single plaque isolation. One isolate, $\Phi K1-5_{(K1-)}$, was further characterized and found to be unable to grow on any of the K1 strains (Table 1).

DNA Sequence of a Putative ΦK5 Tail Gene

Clarke et. al. described a partial sequence of an open reading frame ($ORF_p$) in ΦK5 immediately downstream of the 85 base region common to the three phages (6). We continued sequencing downstream and found the complete open reading frame is 523 amino acids. A BLAST search revealed a small region of sequence similarity with the N-acetylglucosamine-permease IIABC component near the N-terminus. It has no significant sequence similarity with any other entry in the database or any of the tail proteins described here. Sequence was determined an additional 163 bases downstream, at which point the end of the DNA molecule was reached.

FIG. 2 compares the regions encoding tail proteins in all three phages. ΦK1–5 has a K5 lyase protein in the same position as that of ΦK5. ΦK1E has a 111 amino acid open reading frame ($ORF_L$) of unknown function in this position. Immediately downstream all three phages have an intergenic region of 85 bases that has two dyad axis of symmetry. Immediately downstream of this region ΦK1–5 encodes its endosialidase protein, which is in the analogous position as the ΦK1E endosialidase. ΦK5 encodes a 523 amino acid open reading frame ($ORF_p$) in this position. The three phages share sequence similarity upstream of the tail genes. No sequence similarity was noted downstream, and in all three phages the DNA molecule ends downstream.

EXAMPLE 1

Isolation of K1-5

ΦK1–5 was isolated from raw sewage using the plaque technique. Briefly, a 1 L sample of sewage was centrifuged at 6000 rpm in a GSA rotor to remove solid matter and was then passed through a 0.45 micron nitrocellulose filter (Nalgene). 100 μl of filtrate was added to 200 μl of an overnight culture of *E. coli* ATCC 23506 (K5) grown in LB media. 3 ml of melted tempered top agar (5 g/L agar in LB) was added and the mix was plated onto an LB agar plate and incubated at 37° C. overnight. The following day plaques were picked and re-plaqued 3 times to insure pure culture. Final plaque isolates were stored as an agar plug from a Pasteur pipette deposited in 1 ml of SM buffer (10 mM $MgSO_4$, 100 mM NaCl, 0.01% gelatin, 50 mM Tris pH 7.5).

Host range was initially screened by spotting 10 μl of SM buffer containing a plaque plug onto a lawn of an appropriate strain. Host range of interesting phage isolates was further confirmed by the plaque assay. All phage titrations were done by the plaque assay technique.

Large Scale Purification

Phages were prepared by the cesium chloride density gradient method. 1 L of an appropriate host was grown up to and OD 600 of between 0.4 and 0.6 at 37° C. with 200 rpm shaking in LB broth. Phage were added at a moi of 1 phage/100 bacteria, and the culture was allowed to incubate until the OD reached a minimum for 30 min. 10 ml of chloroform was added and allowed to shake for 10 min and was then centrifuged for 20 min at 6000 rpm in GSA rotor to remove cellular debris. The supernatant was collected and 1/10th volume of 5M NaCl and 1/10th w/v of polyethylene glycol was added to precipitate the phage, this was held at 4° C. overnight. The phage were then pelleted by centrifugation at 6000 rpm in a GSA rotor at 4° C. The pellet was resuspended in phosphate buffered saline and CsCl was added to a density of 1.5 g/ml. The sample was spun in Ti80 (Beckman) rotor at 34,000 rpm overnight. The phage band was extracted with a syringe and was dialyzed against phosphate buffered saline (pH 7.4).

DNA Isolation and Sequencing

DNA was isolated from CsCl purified phage by phenol/chloroform extraction. The phage DNA was used directly as a template for DNA sequencing which was carried out by Commonwealth Biotechnologies in Richmond, Va. Both strands were sequenced (of the tail gene region of θK1–5). DNA database searches were done by BLAST (1), and sequence alignments were performed with the Wisconsin Package (9).

Mutagenesis

Cesium purified phage were mutagenized with UV light using a model TM 36 chromatovue transilluminator (UVP, Inc.). Phage were typically exposed for 10–20 sec, which reduced viability by 1000 fold. The mutagenized phage were then amplified on ATCC 23503 or ATCC 23506 and subjected to selection and amplification as described above. Phage were also mutagenized by incubation with 400 mM hydroxylamine until the phage titer was reduced by 100 fold. They were then plated on a double lawn of ATCC 23503 and ATCC 23506. Turbid plaques were picked, replaqued for isolation, and tested for growth against a collection of K1 and K5 E. coli strains.

REFERENCES

1. Altschul, S. F., W., Gish, W., Miller, E. W., Myers, D. J., and Lipman.1990. Basic local alignment search tool. J. Mol. Biol. 215(3): 403–410.
2. Botstein, D. 1980. A theory of modular evolution for bacteriophages. Ann. NY Acad. Sci. 354: 484–490.
3. Brown, J. E., J. F. Klement, and W. T. McAllister. 1986. Sequences of three promoters for the bacteriophage SP6 RNA polymerase. Nucleic Acids Res. (14)8: 3521–3526.
4. Campbell, A., and D. Botstein. 1983. Evolution of the lambdoid phages. In Lambda II. Cold Spring Harbor Laboratory. 365–380.
5. Chandry, P. S., S. C. Moore, J. D. Boyce, B. E. Davidson, and A. J. Hillier. 1997. Analysis of the DNA sequence, gene expression, origin of replication, and modular structure of the Lactococcus lactis lytic bacteriophage sk1. Mol. Microbiol. 26(1): 49–64.
6. Clarke, B. R., F. Esumah, and I. S. Roberts. 2000. Cloning, expression, and purification of the K5 capsular polsaccharide lyase (KflA) from coliphage K5A: evidence for two distinct K5 lyase enzymes. J. Bacteriol. 182(13): 3761–3766.
7. Crawford, J. T. and E. B. Goldberg. 1980. The function of the tail fibers in triggering baseplate expansion of bacteriophage T4. J. Mol. Biol. 139: 679–690.
8. Desiere, F., S. Lucchini, and H. Brussow. 1998. Evolution of Streptococcus thermophilus bacteriophage genomes by modular exchanges followed by point mutations and small deletions and insertions. Virology. 241(2): 345–356.
9. Devereux, J., P. Haeberli, and O. Smithies. 1984. A comprehensive set of sequence analysis programs for the VAX. Nucleic Acids Res. 12(1): 387–395.
10. Gross, R. J., T. Cheasty, and B. Rowe. 1977. Isolation of bacteriophages specific for the K1 polysaccharide antigen of E. coli. J. Clin. Microbiol. 6(6): 548–550.
11. Gupta, D. S., B. Jann, G. Schmidt, J. R. Golecki, I. Ørskov, F. Ørskov, and K. Jann. 1982. Coliphage K5, specific for E. coli exhibiting the capsular K5 antigen. FEMS Microbiol. Lett. 14: 75–78.
12. Gupta, D. S., B. Jann, and K. Jann. 1983. Enzymatic degradation of the capsular K5-antigen of E. coli by coliphage K5. FEMS Microbiol. Lett. 16: 13–17.
13. Haggård-Ljungquist, E., C. Halling, and R. Calendar. 1992. DNA sequences of the tail fiber genes of bacteriophage P2: evidence for horizontal transfer of the tail fiber genes among unrelated bacteriophages. J. Bacteriol. 174(5): 1462–1477.
14. Hanfling, P., A. S. Shashkov, B. Jann, and K. Jann. 1996. Analysis of the enzymatic cleavage (beta elimination) of the capsular K5 polysaccharide of E. coli by the K5-specific coliphage: a reexamination. J. Bacteriol. 178(15): 4747–4750.
15. Hendrix, R. W., M. C. M. Smith, R. N. Burns, M. E. Ford, and G. F. Hatfull. 1999. Evolutionary relationships among diverse bacteriophages and prophages: All the world's a phage. Proc. Natl. Acad. Sci., U.S.A. 96: 2192–2197.
16. Israel, V. 1978. A model for the adsorption of phage P22 to Salmonella typhimurium. J. Gen. Virol. 40: 669–673.
17. Jann, K., and B. Jann. 1987 Polysacharide antigens of E. coli. Rev. Infect. Dis. 9(5): S517–S526.
18. Jeng S. T., S. H. Lay, and H. M. Lai. 1997. Transcription termination by bacteriophage T3 and SP6 RNA polymerases at Rho-independent terminators. Can J. Microbiol. 43(12): 1147–1156.
19. Juhala R. J., M. E. Ford, R. L. Duda, A. Youlton, G. F. Hatfull, and R. W. Hendrix. 2000. Genomic sequences of bacteriophages HK97 and HK022: Pervasive genetic mosaicism in the lambdoid bacteriophages. J. Mol. Biol. 299(1): 27–51.
20. Long, G. S., J. M. Bryant, P. W. Taylor, and J. P. Luzio. 1995. Complete nucleotide sequence of the gene encoding bacteriophage E endosialidase: implications for K1E endosialidase structure and function. Biochem. J. 309: 543–550.
21. Machida, Y., K. Miyake, K. Hattori, S. Yamamoto, M. Kawase, and S. Iijima. 2000. Structure and funtcion of a novel coliphage-associated sialidase. FEMS Microbiol. Lett. 182(2): 333–337.
22. Monod, C., M. Repoila, F. Kutateladze, F. Tetart, and H. M. Krisch. 1997. The genome of the Pseudo T-even bacteriophages, a diverse group that resembles T4. J. Mol. Biol. 267: 237–249.
23. Montag, D., H. Schwarz, and U. Henning. 1989. A component of the side tail fiber of Escherichia coli bacteriophage λ can functionally replace the receptor-recognizing part of a long tail fiber protein of unrelated bacteriophage T4. J. Bacteriol. 171(8): 4378–4384.
24. Montag, D., S. Hashemolhosseini, and U. Henning. 1990. Receptor recognizing proteins of T-even type bacteriophages. The receptor recognizing area of proteins 37 of phages T4 and TuIa and TuIb.
25. Neve, H., K. I. Zenz, F. Desiere, A. Koch, K. J. Heller and H. Brussow. 1998. Comparison of the lysogeny modules from the temperate Streptococcus thermophilus bacteriophages TP-J34 and Sfi21: implications for the modular theory of phage evolution. Virology, 241(1): 61–72
26. Nimmich, W., G. Schmidt, and U. Krallmann-Wenzel. 1991. Two different E.coli capsular polysaccharide depolymerases each associated with one of the coliphage ΦK5 and ΦK20. FEMS Microbiol. Lett. 82: 137–142.
27. Nimmich, W., U. Krallman-Wenzel, B. Muller, and G. Schmidt. 1992. Isolation and characterization of bacteriophages specific for capsular antigens K3, K7, K12, and 27. K13 of *E. coli*. Int. J. Med. Microbiol. Virol. Parasitol. Infect. Dis. 276(2): 213–220.
28. Nimmich, W. 1994. Detection of *E. coli* K95 strains by bacteriophages. J. Clin. Microbiol. 32(11): 2843–2845.
29. Petter, J. G., and E. R. Vimr. 1993. Complete nucleotide sequence of the bacteriophage K1F tail gene encoding Endo-N-Acylneuraminidase (Endo-N) and comparison to an endo-N homolog in bacteriophage PK1E. J. Bacteriol. 175(14): 4354–4363.
30. Seckler, R. 1998. Folding and function of repetitive structure in the homotrimeric phage P22 tailspike protien. J. Struct. Biol. 122: 216–222.
31. Schicklmaier, P., and H. Schmeiger. 1997. Sequence comparison of the genes for immunity, DNA replication, and cell lysis of the P22-related Salmonella phages ES18 and L. Gene. 195: 93–100.
32. Silver, R. P., and E. R. Vimr. 1990. Polysialic acid capsule of *E. coli* K1. in The Bacteria, vol. 11. Molecular basis of bacterial pathogenesis. pp 39–60. Academic Press, Inc., New York.
33. Steven, A. C., B. L. Trus, J. V. Maizel, M. Unser, D. A. D. Parry, J. S. Wall, J. F. Hainfield, and W. F. Studier. 1988. Molecular substructure of a viral receptor-recognition protein. J. Mol. Biol. 200(2): 351–365.
34. Szybalski, W., and E. H. Szybalski. 1974. Visualization of the evolution of viral genomes. In Viruses, evolution and cancer. pp. 563–582. Academic Press, New York.
35. Tetart, F., F. Repoila, C. Monod, and H. M. Krisch. 1996. Bacteriophage T4 host range is expanded by duplications of a small domain of the tail fiber adhesion. J. Mol. Biol. 258(5): 726–731.
36. Tetart, F., C. Desplats, and H. M Krisch. 1998 Genome plasticity in the distal tail fiber locus of the T-even bacteriophage: recombination between conserved motifs swaps adhesion specificity. J. Mol. Biol. 282(3): 543–556.
37. Tomlinson, S., and P. W. Taylor. 1985. Neuraminidase asssociated with coliphage E that specifically depolymerizes the *E. coli* K1 capsular polysaccharide. J. Virol. 55(2): 374–378.
38. Yin, J. 1993. Evolution of bacteriophage T7 in a growing plaque. J. Bacteriol. 175(5): 1272.

While the present invention has been described in some detail for purposes of clarity and understanding, one skilled in the art will appreciate that various changes in form and detail can be made without departing from the true scope of the invention. All figures, tables, and appendices, as well as patents, applications, and publications, referred to above, are hereby incorporated by reference.

What is claimed is:
1. Isolated or purified bacteriophage ΦK1–5.
2. Isolated bacteriophage ΦK1–5.
3. Purified bacteriophage ΦK1–5.

* * * * *